(12) United States Patent
Forsell

(10) Patent No.: US 12,042,388 B2
(45) Date of Patent: Jul. 23, 2024

(54) HIP JOINT DEVICE AND METHOD

(71) Applicant: Peter Forsell, Lund (SE)

(72) Inventor: Peter Forsell, Lund (SE)

( * ) Notice: Subject to any disclaimer, the term of this patent is extended or adjusted under 35 U.S.C. 154(b) by 595 days.

(21) Appl. No.: 17/149,837

(22) Filed: Jan. 15, 2021

(65) Prior Publication Data

US 2021/0205088 A1    Jul. 8, 2021

Related U.S. Application Data

(63) Continuation of application No. 15/850,042, filed on Dec. 21, 2017, now Pat. No. 10,918,489, which is a
(Continued)

(30) Foreign Application Priority Data

| Jul. 10, 2009 | (SE) | 0900957-2 |
|---|---|---|
| Jul. 10, 2009 | (SE) | 0900958-0 |
| Jul. 10, 2009 | (SE) | 0900959-8 |
| Jul. 10, 2009 | (SE) | 0900960-6 |
| Jul. 10, 2009 | (SE) | 0900962-2 |
| Jul. 10, 2009 | (SE) | 0900963-0 |
| Jul. 10, 2009 | (SE) | 0900965-5 |
| Jul. 10, 2009 | (SE) | 0900966-3 |
| Jul. 10, 2009 | (SE) | 0900968-9 |
| Jul. 10, 2009 | (SE) | 0900969-7 |
| Jul. 10, 2009 | (SE) | 0900970-5 |
| Jul. 10, 2009 | (SE) | 0900972-1 |
| Jul. 10, 2009 | (SE) | 0900973-9 |
| Jul. 10, 2009 | (SE) | 0900974-7 |
| Jul. 10, 2009 | (SE) | 0900976-2 |
| Jul. 10, 2009 | (SE) | 0900978-8 |
| Jul. 10, 2009 | (SE) | 0900981-2 |

(51) Int. Cl.
*A61F 2/36*    (2006.01)
*A61F 2/32*    (2006.01)
(Continued)

(52) U.S. Cl.
CPC ............... *A61F 2/32* (2013.01); *A61F 2/34* (2013.01); *A61F 2/3609* (2013.01);
(Continued)

(58) Field of Classification Search
CPC .. A61F 2/32; A61F 2/34; A61F 2/3609; A61F 2002/3233
See application file for complete search history.

(56) References Cited

U.S. PATENT DOCUMENTS

| 4,159,544 A * | 7/1979 | Termanini | A61F 2/32 623/22.14 |
| 2003/0236572 A1* | 12/2003 | Bertram, III | A61F 2/32 623/18.12 |

\* cited by examiner

*Primary Examiner* — Brian A Dukert

(57) ABSTRACT

The invention relates to a method of installing a medical device for reducing the risk of permanent damage to a hip joint of a human patient, said method comprising the steps of: exposing the hip joint through a surgical or arthroscopic procedure, fixating a first piece of said medical device to the femoral bone, fixating a second piece of said medical device to the pelvic bone, placing said first piece in connection with said second piece, holding said first piece to said second piece using a releasing member, and releasing said first piece from said second piece when a pre-determined strain is placed on said releasing member.

15 Claims, 16 Drawing Sheets

Related U.S. Application Data continuation of application No. 15/055,802, filed on Feb. 29, 2016, now Pat. No. 9,848,988, which is a continuation of application No. 13/383,276, filed as application No. PCT/SE2010/050821 on Jul. 12, 2010, now Pat. No. 9,271,838.

(60) Provisional application No. 61/229,743, filed on Jul. 30, 2009, provisional application No. 61/229,745, filed on Jul. 30, 2009, provisional application No. 61/229,746, filed on Jul. 30, 2009, provisional application No. 61/229,747, filed on Jul. 30, 2009, provisional application No. 61/229,748, filed on Jul. 30, 2009, provisional application No. 61/229,751, filed on Jul. 30, 2009, provisional application No. 61/229,752, filed on Jul. 30, 2009, provisional application No. 61/229,755, filed on Jul. 30, 2009, provisional application No. 61/229,761, filed on Jul. 30, 2009, provisional application No. 61/229,767, filed on Jul. 30, 2009, provisional application No. 61/229,778, filed on Jul. 30, 2009, provisional application No. 61/229,786, filed on Jul. 30, 2009, provisional application No. 61/229,789, filed on Jul. 30, 2009, provisional application No. 61/229,796, filed on Jul. 30, 2009, provisional application No. 61/229,735, filed on Jul. 30, 2009, provisional application No. 61/229,738, filed on Jul. 30, 2009, provisional application No. 61/229,739, filed on Jul. 30, 2009.

(51) Int. Cl.
    *A61F 2/34*     (2006.01)
    *A61F 2/30*     (2006.01)

(52) U.S. Cl.
    CPC .............. *A61F 2002/30079* (2013.01); *A61F 2002/30594* (2013.01); *A61F 2002/3233* (2013.01); *A61F 2002/3611* (2013.01)

ained HIP JOINT DEVICE AND METHOD

This application is a continuation of U.S. patent application Ser. No. 15/850,042 filed Dec. 21, 2017, which is a continuation of U.S. patent application Ser. No. 15/055,802 filed Feb. 29, 2016, which is a continuation of U.S. patent application Ser. No. 13/383,276 filed Jan. 10, 2012, which is the U.S. national phase of International Application No. PCT/SE2010/050821, filed Jul. 12, 2010, which designates the US and claims priority to Swedish Application Nos. 0900981-2; 0900957-2, 0900959-8, 0900960-6, 0900962-2; 0900963-0; 0900965-5; 0900966-3; 0900968-9; 0900969-7; 0900970-5; 0900972-1; 0900973-9; 0900974-7; 0900976-2; 0900978-8 and 0900958-0, all filed Jul. 10, 2009, and which claims the benefit of U.S. Provisional Nos. 61/229,738; 61/229,739; 61/229,743; 61/229,745; 61/229,746; 61/229,747; 61/229,748; 61/229,751; 61/229,752; 61/229,755: 61/229,761; 61/229,767; 61/229,778: 61/229,786; 61/229,789; 61/229,796 and 61/229,735 all filed on Jul. 30, 2009, respectively, the entire contents of each of which are hereby incorporated by reference.

TECHNICAL FIELD

The invention relates generally to hip joint prosthesis.

BACKGROUND

Hip joint Osteoarthritis is a syndrome in which low-grade inflammation results in pain in the hip joints, caused by abnormal wearing of the Cartilage that acts as a cushion inside if the hip joint. This abnormal wearing of the cartilage also results in a decrease of the joints lubricating fluid called Synovial fluid. Hip joint Osteoarthritis is estimated to affect 80% of all people over 65 years of age, in more or less serious forms.

The present treatment for hip osteoarthritis comprises NSAID drugs, local injections of Hyaluronic acid or Glucocorticoid to help lubricating the hip joint, and replacing parts of the hip joint with a prosthesis through hip joint surgery.

The replacing of parts of the hip joint is one of the most common surgeries to date performed at hundreds of thousands of patients in the world every year. The most common method comprises placing a metal prosthesis in Femur and a plastic bowl in Acetabulum. This operation is done through an incision in the hip and upper thigh and through Fascia Lata and the lateral muscles of the thigh. To get access to the joint, the supporting Fibrous Capsule attached to Femur and Ilium needs to be penetrated, making it difficult to get a fully functional joint after the surgery. Femur is then cut at the neck with a bone saw and the prosthesis is placed in femur either with bone cement or without. Acetabulum is slightly enlarged using an Acetabular reamer, and the plastic bowl is positioned using screws or bone cement.

The complications after hip joint surgery includes dislocation of the hip joint and loosening of the prosthesis from its fixation in the femoral bone. The loosening and/or dislocation of the prosthesis could be induced by an abnormal strain being placed on the hip joint from e.g. the patient falling or making a rapid movement of the hip. A completely fixed hip joint prosthesis, without the possibility to dislocate would increase the risk of the prosthesis loosening from its fixation in the femoral bone, since the entire strain is then placed on the femoral bone.

A hip joint prosthesis that could reduce the complications after hip joint surgery would therefore be desirable.

SUMMARY

A medical device for implantation in a hip joint of a patient is provided. The medical device comprises a first and second piece and a releasing member adapted to, in a first state hold the first piece attached to the second piece, and in a second state release the first piece from the second piece. The releasing member is adapted to change from the first state to the second state when a pre-determined strain is placed on the releasing member.

According to one embodiment the first piece comprises a ball shaped piece, adapted to replace at least the surface of the caput femur in the hip joint.

According to one embodiment the second piece comprises a bowl shaped piece, adapted to replace at least the acetabulum surface in the hip joint.

According to another embodiment the first piece comprises a ball shaped piece and the second piece comprises a bowl shaped piece, and the ball shaped piece is adapted to be placed in the bowl shaped piece to replace a functioning hip joint, thereby creating an entirely artificial hip joint. The ball shaped piece could be adapted to be fixated in the bowl shaped piece using the releasing member.

The releasing member according to any of the embodiments could be adapted to non-invasively change from the first state to the second state and from the second state to the first state, when a pre-determined strain is placed on said releasing member. Thereby, if dislocated the hip joint can be reinstated without the need of a surgical procedure.

The at least one of the first and second piece could comprise at least two parts adapted to be in contact with each other when the medical device is implanted in the patient.

The first and/or the second piece could be adapted to be introduced through a hole in the pelvic bone of the patient.

According to one embodiment the at least two pieces are adapted to be mechanically fixated to each other after the at least two pieces have been introduced into the hip joint through a hole in the pelvic bone of the patient.

Releasing Member

According to one embodiment the first piece of the medical device comprises the releasing member. Which could be a ball shaped piece of the medical device comprising the releasing member. According to another embodiment the second piece of the medical device comprises the releasing member. Which could be a bowl shaped piece of the medical device comprising the releasing member.

According to another embodiment the releasing member comprises an elastic portion, which in turn could comprise an elastic material.

According to yet another embodiment the releasing member comprises a bendable and/or flexible and/or compressible portion. It is furthermore conceivable that the releasing member comprises a movable portion or movable part.

In the embodiments where the medical device comprises an elastic portion, the elastic portion could comprise a spring and/or an elastic band, which could be adapted to at least partly encircle the ball shaped piece and thereby holding the ball shaped piece in the bowl shaped piece. The elastic band could further be adapted to be placed between the ball shaped piece and the bowl shaped piece.

According to yet another embodiment the releasing member comprises a magnet adapted to hold the first piece to the second piece.

According to another embodiment the releasing member comprises a rupture device adapted to fail at a pre-determined strain, for releasing the first piece from the second piece. The rupture device could comprise a rupture band, which could be adapted to at least partly encircle the ball shaped piece. The rupture band could, according to one embodiment be placed between the ball shaped piece and the bowl shaped piece, and could comprise a rupture pin.

The releasing member could comprise multiple holding members, and the holding members or holding member could be adapted to slide against said first piece and/or adapted to roll against said first piece. The holding member could comprise a ball shaped holding member.

First Piece

According to one embodiment, the first piece comprises at least two parts adapted to be in contact with each other when the medical device is implanted in the patient.

The first piece, according to any of the embodiments, could be adapted to be introduced through a hole in the pelvic bone of the patient.

According to one embodiment, one of the at least two parts is adapted to be mechanically fixated to the second of the at least two parts after the at least two parts have been introduced into the hip joint through a hole in the pelvic bone of the patient.

The first piece could comprise a flexible portion and/or an elastic portion adapted to enable the medical device to be inserted through a hole in the pelvic bone. The elastic portion could enable the compression of the first piece in at least one direction.

The first piece could comprise a first area and a second area, the first area could comprise a first material adapted to be elastic and the second area could comprise a second material adapted to be elastic, and the first material could be adapted to be more elastic than the second material.

Second Piece

According to one embodiment the second piece comprises at least two parts adapted to be in contact with each other when the medical device is implanted in the patient. The second piece could be adapted to be introduced through a hole in the pelvic bone of the patient.

According to another embodiment, one of said at least two parts could be adapted to be mechanically fixated to a second of the at least two parts after the at least two parts have been introduced into the hip joint through a hole in the pelvic bone of the patient.

According to yet another embodiment the medical device comprises at least a three-dimensionally curved hip joint surface comprising: an inner surface, and an outer surface. The inner surface comprises six different points: a first point, a second point, a third point, a fourth point, a fifth point, and a sixth point, all points located on different places along a length axis of the inner surface. A first straight line, reaching from said first point to said second point is parallel to a second straight line reaching from said third point to said fourth point, which in turn is parallel to a third straight line reaching from said fifth point to said sixth point. Furthermore, the first and third straight lines are shorter than said second straight line, and said second straight line is positioned between said first and said third straight lines.

The medical device could further comprise a calibration member for calibrating the pre-determined strain required for said releasing member to change from said first state to said second state. The calibration member could be a calibration screw.

The normal hip joint have a collum femur, having an axial distribution leading to a caput femur, having a substantially ball shaped configuration with a maximum diameter substantially perpendicular to the centre axis of the prolongation of said axial distribution of said collum femur. The caput femur is placed in a bowl shaped acetabulum creating the hip joint. The bowl shaped acetabulum have an opening and a second axial distribution with a center axis from the center of the bottom of the acetabulum bowl and following the center of the bowl towards the opening and caput femur, wherein the acetabulum have a maximum diameter substantially perpendicular to the center axis of the second axial distribution of the acetabulum. The prolongation of the centre axis of the axial distribution is identical to the center axis of the second axial distribution, when the caput femur is in a centered and symmetrical position in the acetabulum bowl. The medical device comprises two artificial hip joint surfaces, the first piece comprises; the artificial hip joint surface comprising, an artificial caput femur surface adapted to at least partly replace and replacing the joint surface of the caput femur, on the opposite side of collum femur, and adapted to, when mounted in the joint, be placed in the acetabulum bowl or an artificial replacement therefore. The artificial caput femur surface, comprising at least one first beyond part of the surface adapted to cover and/or going into the bone of said caput femur on at least a part of said caput femur beyond the maximum diameter of said caput femur, away from said acetabulum bowl towards said collum femur, when mounted on said caput femur in its functional position in the joint. The at least one first beyond part is adapted to have a closest perpendicular distance to said center axis, being smaller than the distance between the periphery of said maximum diameter of said caput femur and said center axis, thus adapted to create and creating a more stable position of said artificial caput femur surface when mounted on said caput femur in said functional position. The beyond part comprises at least a part of the releasing member.

The normal hip have a collum femur having an axial distribution leading to a caput femur having a substantially ball shaped configuration with a maximum diameter substantially perpendicular to the centre axis of the prolongation of said axial distribution of said collum femur. The caput femur is placed in a bowl shaped acetabulum creating the hip joint. The bowl shaped acetabulum have an opening and a second axial distribution with a center axis from the center of the bottom of said acetabulum bowl and following the center of said bowl towards the opening and caput femur. The acetabulum have a maximum diameter substantially perpendicular to the center axis of said second axial distribution of the acetabulum, the prolongation of the center axis of the axial distribution is identical to the center axis of the second axial distribution, when the caput femur is in a centered and symmetrical position in the acetabulum bowl. The medical device comprises two artificial hip joint surfaces, the artificial hip joint surface comprising, an artificial acetabulum surface adapted to at least partly replace and replacing the joint surface of the acetabulum, and adapted to be placed onto the caput femur, or an artificial replacement therefore, when mounted in the hip joint. The artificial acetabulum surface, comprises at least one first beyond part of the surface adapted to cover at least a part of the caput femur or the artificial replacement therefore beyond the maximum diameter of the acetabulum, away from the acetabulum bowl towards the collum femur, when mounted onto the caput femur or an artificial replacement therefore, in its functional position in the hip joint. The at least one first beyond part adapted to have a closest perpendicular distance to said centre axis, being smaller than the distance between the periphery of said maximum diameter of said artificial acetabulum surface and said centre axis, thus adapted to create and creating a more stable position of the artificial acetabulum surface when mounted on the caput femur or an artificial replacement therefore, in said functional position in said hip joint. The first beyond part comprises the releasing member.

The releasing member, according to any of the embodiments could comprise an elastic portion and/or a bendable portion and/or a flexible portion and/or a compressible portion and/or a movable portion and/or a movable part, for enabling the releasing of the first piece from the second piece.

A method of installing a medical device according to any of the embodiments is further provided, the method comprises the steps of: exposing the hip joint through a surgical or arthroscopic procedure, fixating said first piece of said medical device to the femoral bone, fixating said second piece of said medical device to the pelvic bone, placing said first piece in connection with said second piece, and holding said first piece to said second piece using said releasing member.

According to one embodiment, the step of holding the first piece to the second piece comprises holding the first piece to the second piece using an elastic member.

According to one embodiment, the step of holding the first piece to the second piece comprises holding the first piece to the second piece using a rupturing member.

According to one embodiment, the step of holding the first piece to the second piece comprises holding the first piece to the second piece using a spring loaded member.

According to one embodiment, the step of holding the first piece to the second piece comprises holding the first piece to the second piece using an elastic band.

According to one embodiment, the step of holding the first piece to the second piece comprises holding the first piece to the second piece using a rupturing band.

According to one embodiment, the second piece comprising an bowl shaped inner surface, adapted to receive said first piece being ball shaped to be at least partly placed inside said inner surface, wherein: said inner surface comprises an equator line, being the largest circular circumference of said inner surface, said at least one extending portion of said inner surface passes beyond said equator line, such that the end portion of a contacting portion of said inner surface, the most distal portion of said inner surface adapted to contact the prosthetic caput femur, when the inner surface is placed symmetrically onto the prosthetic caput femur, forms a circular extension line parallel to said equator line having a smaller circumference than said equator line, and said at least one extending portion is constructed according to at least one of the following alternatives; a) circumferentially extends discontinuously along said equator line having enough circumferential distance lacking any extending portion and b) extends with different distal extension in different extending portions or part of such portion of said circumferential extension.

According to one embodiment, said second piece comprising a bowl shaped inner surface, adapted to receive said first piece being ball shaped to be at least partly placed inside said inner surface, wherein: said inner surface comprises an equator line, being the largest circular circumference of said inner surface, said at least one extending portion of said inner surface passes beyond said equator line, such that the end portion of a contacting portion of said inner surface, the most distal portion of said inner surface adapted to contact a prosthetic caput femur, when the inner surface is placed symmetrically onto the prosthetic caput femur, forms a circular extension line parallel to said equator line having a smaller circumference than said equator line, and said at least one extending portion extends with different distal extension over the circumferential extension, thus adapted to restrict movements clearly different in different directions of movement, due to different distal extension of different extending portions in said circumferential extension.

According to one embodiment, said second piece comprising an bowl shaped inner surface, adapted to receive said first piece being ball shaped to be at least partly placed inside said inner surface, wherein: said inner surface comprises an equator line, being the largest circular circumference of said inner surface, at least one extending portion of said inner surface passes beyond said equator line, such that the end portion of a contacting portion of said inner surface, the most distal portion of said inner surface adapted to contact a prosthetic caput femur, when the inner surface is placed symmetrically onto the prosthetic caput femur, forms a circular extension line parallel to said equator line having a smaller circumference than said equator line, and part of said at least one extending portion extends with different distal extension over the circumferential extension, thus adapted to restrict movements clearly different in different directions of movement, due to different distal extension of different parts of such extending portion in said circumferential extension.

According to one embodiment, the releasing member comprising a locking member for locking the second piece being an artificial replacement of an acetabulum in a hip joint to clasp the second piece being an artificial replacement of caput femur, when implanted in a hip joint of a patient, wherein said locking member is adapted to in situ assist in the fixation of the medical device, wherein: said inner surface comprises an equator line, being the largest circular circumference of said inner surface, at least one extending portion of said inner surface passes beyond said equator line, such that the end portion of a contacting portion of said inner surface, the most distal portion of said inner surface adapted to contact the artificial replacement of caput femur, when the inner surface is placed symmetrically onto the prosthetic caput femur, forms a circular extension line parallel to said equator line having a smaller circumference than said equator line, said locking member is adapted to lock said artificial replacement of caput femur such that it remains clasped and restrained in said inner surface until released by said releasing member, and said locking member is adapted to lock said at least one extension portion, when implanted, having at least the end portion of the extension portion radially fixed within said circular extension line.

According to one embodiment, the said locking member is adapted to lock in at least a first and second locking position.

According to one embodiment, said locking member is adapted to lock in at least a first and a second locking position, and wherein said locking member is adapted to; in said first locking position, lock the artificial acetabulum inner surface having at least one extending portion, to a first size artificial caput femur, and in said second locking position, lock said artificial actabulum inner surface, to a second smaller size artificial caput femur.

The hip joint has a collum femur, having a first axial distribution leading to a caput femur, wherein said collum femur is placed distal to the caput femur, a center axis of the collum and caput femur in line with the first axial distribution being the caput femur center axis, wherein the caput femur has a substantially ball shaped configuration with an outer maximum radius perpendicular to the caput femur center axis, the caput femur being placed in a bowl shaped acetabulum, having an opening, wherein the bowl shaped acetabulum has a second axial distribution with an acetabulum center axis from the center of the bottom of the acetabulum bowl and following the center of the bowl towards the center of the opening of the bowl, towards the caput femur, wherein the acetabulum bowl has an inner maximum radius perpendicular to the acetabulum center axis, wherein the caput femur center axis is in line/aligned with the acetabulum center axis, in a special centered position, when the caput femur is placed; aligned, centered and symmetrical in the acetabulum bowl in the hip joint, the aligned center axis is defined as the hip joint center axis, wherein the caput femur and the acetabulum has one hip joint surface each, placed towards and contacting each other, wherein the hip joint surfaces carrying weight in the hip joint are the weight carrying surfaces, wherein the outer maximum radius of the caput femur is forming a circular extending, maximum caput femur radius circle, extending perpendicular to the hip joint center axis, defining a maximum caput femur radius cross-section perpendicular to the hip joint center axis, wherein: said medical device comprises at least one artificial hip joint surface, adapted to at least partly replace at least one of the hip joint surfaces, said artificial hip joint surface at least partly being hollow and having an inner and outer surface, wherein said artificial hip joint surface has an artificial hip joint surface center axis aligned with the hip joint center axis when the hip joint is placed in the special centered position, when at least one of said artificial hip joint surfaces is implanted in the hip joint, with the caput femur or an artificial caput femur surface placed; aligned, centered and symmetrical in the acetabulum bowl or an artificial acetabulum surface in the hip joint, wherein said medical device comprises a central part and a surrounding part, the central part being aligned with the artificial hip joint surface center axis and the surrounding part surrounding the surface of the caput femur or an artificial caput femur surface not including the central part, wherein the caput femur or an artificial caput femur surface, has a maximum caput femur radius cross-section, in which the outer maximum radius of the caput femur or said artificial caput femur surface is forming a circular extending maximum caput femur or artificial caput femur radius circle, extending perpendicular to the hip joint center axis, defining the maximum caput femur radius cross-section perpendicular to the hip joint center axis or perpendicular to said artificial hip joint surface center axis, when the hip joint is placed in said special centered position, wherein the surrounding part of said at least one artificial hip joint surface comprises at least one first extending portion of the artificial hip joint surface for extending in distal direction at least partly beyond the maximum caput femur radius cross-section, when the hip joint is placed in said special centered position, when at least one of the artificial hip joint surfaces is implanted in the hip joint, wherein said at least one first beyond part is adapted to have a closest perpendicular distance to said artificial hip joint surface center axis, being smaller than an inner maximum distance, extending perpendicularly from said artificial hip joint surface center axis to said inner surface of said artificial hip joint surface, when the hip joint is placed in the above mentioned special centered position and said artificial hip joint surface is placed in a functional position in the hip joint, thus adapted to create and creating a more stable position of said artificial hip joint surface when mounted in the hip joint.

The hip joint has a caput femur hip joint surface partly being the contacting surface of the hip joint, the hip joint further having a collum femur, having a first axial distribution leading to a caput femur, wherein a center axis of the first axial distribution of the collum femur and the caput femur, being the caput femur center axis, wherein the collum femur is placed more distal than caput femur, wherein; said medical device comprises an artificial caput femur surface being hollow, having a major opening adapted to be directed towards the caput femur or a surgically modified caput femur, wherein said artificial caput femur surface is adapted to replace a caput femur hip joint surface, wherein said artificial caput femur surface further having; a medical device caput center axis passing through said major opening, being aligned with the caput femur center axis, when said medical device is implanted in a functional position in the hip joint, wherein said medical device comprises a central part and a surrounding part, the central part being aligned with the medical device center axis and the surrounding part surrounding the surface of the caput femur or the surgically modified caput femur not including the central part, and wherein said medical device further comprising an inner surface adapted to have a first distal distance extending perpendicularly from said medical device caput center axis to said inner surface of the surrounding part of said artificial caput femur surface, said first distal distance being shorter than a second proximal distance extending perpendicularly from said medical device caput center axis to said inner surface of said artificial caput femur surface, said second proximal distance extending from a more proximal position on said medical device caput center axis than said first distal distance, being the second proximal distance, when said artificial caput femur surface is implanted in said functional position in the hip joint.

The hip joint has an acetabulum, being a bowl shaped contacting surface of the hip joint comprising a substantially circular major opening in distal direction of the acetabulum in the hip joint and a bottom center point in said bowl shaped acetabulum proximally in the hip joint, wherein an acetabulum center axis extends from the bottom point through the center point of the substantially circular opening, wherein the acetabulum has a weight carrying surface contacting a ball shaped caput femur located in the acetabulum bowl in the hip joint, wherein the caput femur is connected to the collum femur, and the collum femur has a center axis aligned with a caput femur center axis, wherein; said medical device comprises an artificial acetabulum surface adapted to replace the weight carrying surface of the acetabulum, wherein said artificial acetabulum surface is hollow and has a major acetabulum opening adapted to be directed towards the caput femur or an artificial replacement of at least the surface of the caput femur, wherein said artificial acetabulum surface is adapted to receive a caput femur or an artificial replacement of at least the surface of the caput femur, in said hollow artificial acetabulum surface, when implanted in the hip joint, said artificial acetabulum surface having; a medical device acetabulum center axis, adapted to be aligned with the acetabulum center axis, when said artificial acetabulum surface is placed in the hip joint, and an inner surface adapted to have a first distal distance extending perpendicularly from said medical device acetabulum center axis, to said inner surface of said artificial acetabulum surface, said first distal distance being shorter than a second proximal distance extending perpendicularly from said medical device acetabulum center axis to said inner surface of said artificial acetabulum surface, said second proximal distance extending from a more proximal position on said medical device acetabulum center axis than said first distal distance, when said artificial acetabulum surface is implanted functionally in the hip joint, wherein said artificial acetabulum surface is adapted to receive in the hollow artificial acetabulum surface the caput femur or an artificial replacement of at least the surface of the caput femur, when implanted in the hip joint, for achieving a functional hip joint.

According to one embodiment, said at least one of extending portion is adapted to have at least one of its shape or position such that the restriction of movement range of the hip joint, in degrees from maximal movement, is restricted more in at least one predefined direction than in any other direction, when implanted.

According to one embodiment, the second piece comprising an bowl shaped inner surface, adapted to receive said first piece being ball shaped to be at least partly placed inside said inner surface, wherein: said inner surface comprises an equator line, being the largest circular circumference of said inner surface, at least one extending portion of said inner surface passes beyond said equator line, such that the end portion of a contacting portion of said inner surface, the most distal portion of said inner surface adapted to contact the first ball shaped piece, when the inner surface is placed symmetrically onto the first piece, forms a circular extension line parallel to said equator line having a smaller circumference than said equator line, and wherein said extending portion is restricting the motion range of the hip joint, and wherein said extending portion is adapted to be placed or shaped such that at least one of adduction, abduction, flexion, extension, a combination of flexion and adduction or abduction, a combination of extension and adduction or abduction, rotation in, rotation out, and any combination of rotation in or out and the other described movements, is restricted more degrees from maximal movement than any of the other movements.

Please note that any embodiment or part of embodiment, feature, method, associated system, part of system described herein or in the associated figures may be combined in any way.

BRIEF DESCRIPTION OF THE DRAWINGS

The invention is now described, by way of example, with reference to the accompanying drawings, in which.

DETAILED DESCRIPTION

Figure 1:
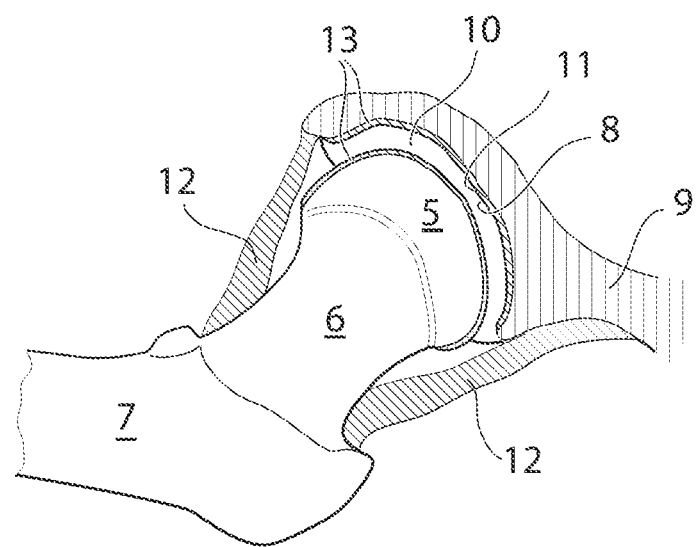
FIG. 1 shows the hip joint in section.

Elasticity is to be understood as a materials ability to deform in an elastic way.

Elastic deformation is when a material deforms under stress (e.g. external forces), but returns to its original shape when the stress is removed. A more elastic material is to be understood as a material having a lower modulus of elasticity. The elastic modulus of an object is defined as the slope of its stress-strain curve in the elastic deformation region. The elastic modulus is calculated as stress/strain, where stress is the force causing the deformation, divided by the area to which the force is applied; and strain is the ratio of the change caused by the stress.

Stiffness is to be understood as the resistance of an elastic body to deformation by an applied force.

Functional hip movements are to be understood as movements of the hip that at least partly correspond to the natural movements of the hip. On some occasions the natural movements of the hip joint might be somewhat limited or altered after hip joint surgery, which makes the functional hip movements of a hip joint with artificial surfaces somewhat different than the functional hip movements of a natural hip joint.

The functional position of an implantable medical device or prosthesis is the position in which the hip joint can perform functional hip movements. The final position is to be understood as a functional position in which the medical device needs no further position change.

Biocompatible material is to be understood as being a material with low level of immune response. Biocompatible materials are sometimes also referred to as biomaterials. Analogous is biocompatible metals a biocompatible metal with low immune response such as titanium or tantalum. The biocompatible metal could also be a biocompatible alloy comprising at least one biocompatible metal.

Form fitting is to be understood as an element having a part or section which is adapted to enable a mechanical connection of said element to at least one other element using said part or section. Form fitted structure is a structure of an element which enables form fitting.

The medical device according to any of the embodiments could comprise at least one material selected from a group consisting of: polytetrafluoroethylene (PTFE), perfluoroalkoxy (PFA) and fluorinated ethylene propylene (FEP). It is furthermore conceivable that the material comprises a metal alloy, such as cobalt-chromium-molybdenum or titanium or stainless steel, or polyethylene, such as cross-linked polyethylene or gas sterilized polyethylene. The use of ceramic material is also conceivable, in the contacting surfaces or the entire medical device such as zirconium or zirconium dioxide ceramics or alumina ceramics. The part of the medical device in contact with human bone for fixation of the medical device to human bone could comprise a poorhouse structure which could be a porous micro or nano-structure adapted to promote the growth-in of human bone in the medical device for fixating the medical device. The porous structure could be achieved by applying a hydroxy-apatite (HA) coating, or a rough open-pored titanium coating, which could be produced by air plasma spraying, a combination comprising a rough open-pored titanium coating and a HA top layer is also conceivable. The contacting parts could be made of a self lubricated material such as a waxy polymer, such as PTFE, PFA, FEP, PE and UHMWPE, or a powder metallurgy material which could be infused with a lubricant, which preferably is a biocompatible lubricant such as a Hyaluronic acid derivate. It is also conceivable that the material of contacting parts or surfaces of the medical device herein is adapted to be constantly or intermittently lubricated. According to some embodiments the parts or portions of the medical device could comprise a combination of metal materials and/or carbon fibers and/or boron, a combination of metal and plastic materials, a combination of metal and carbon based material, a combination of carbon and plastic based material, a combination of flexible and stiff materials, a combination of elastic and less elastic materials, Corian or acrylic polymers.

In the following a detailed description of preferred embodiments of the present invention will be given. In the drawing figures, like reference numerals designate identical or corresponding elements throughout the several figures. It will be appreciated that these figures are for illustration only and are not in any way restricting the scope of the invention. Thus, any references to direction, such as "up" or "down", are only referring to the directions shown in the figures. Also, any dimensions etc. shown in the figures are for illustration purposes.

FIG. 1 shows the hip joint of a human patient in section. The hip joint comprises a caput femur 5, or an artificial replacement therefore, placed at the very top of collum femur 6 which is the top part of the femoral bone 7. The caput femur 5, is in connection with the acetabulum 8 which is a bowl shaped part of the pelvic bone 9. Both the caput femur surface 10 and the acetabulum surface 11 is covered with articular cartilage 13 which acts as a cushion in the hip joint. In patients with hip joint osteoarthritis, this articular cartilage 13 is abnormally worn down due to a low grade inflammation. The hip joint is surrounded by the hip joint capsule 12 which provides support for the joint and hinders luxation. After conventional hip joint surgery, penetrating the hip joint capsule 12, the capsule 12 is dramatically weakened due to the limited healing possibilities of its ligament tissue. By performing hip joint surgery without damaging the hip joint capsule 12 the patient can fully recover and place equal amount of strain on an artificial joint as is possible on a natural one.

Figure 2:
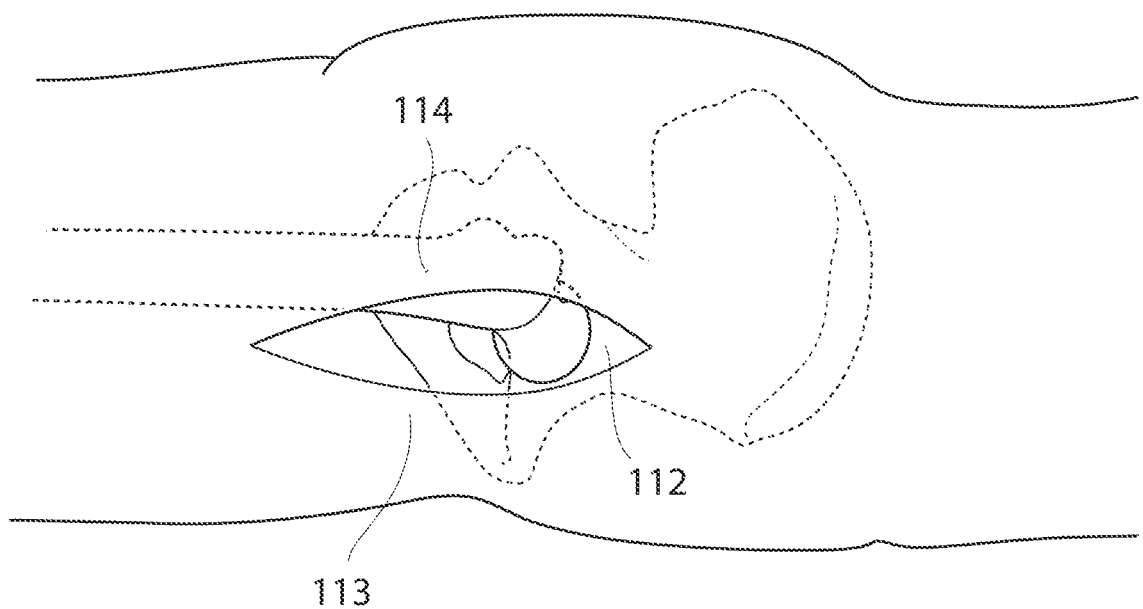
FIG. 2 shows the first step in a conventional hip joint surgery.

FIG. 2 shows a lateral view of a conventional hip joint surgery where an incision 112 is made in the thigh 113 enabling the surgeon to reach the femoral bone 7 on which the caput femur 5 is located. The femoral bone 7 is then extracted from the hip joint capsule 12 exposing the caput femur 5, which is replaced or resurfaced during the operation.

Figure 3:
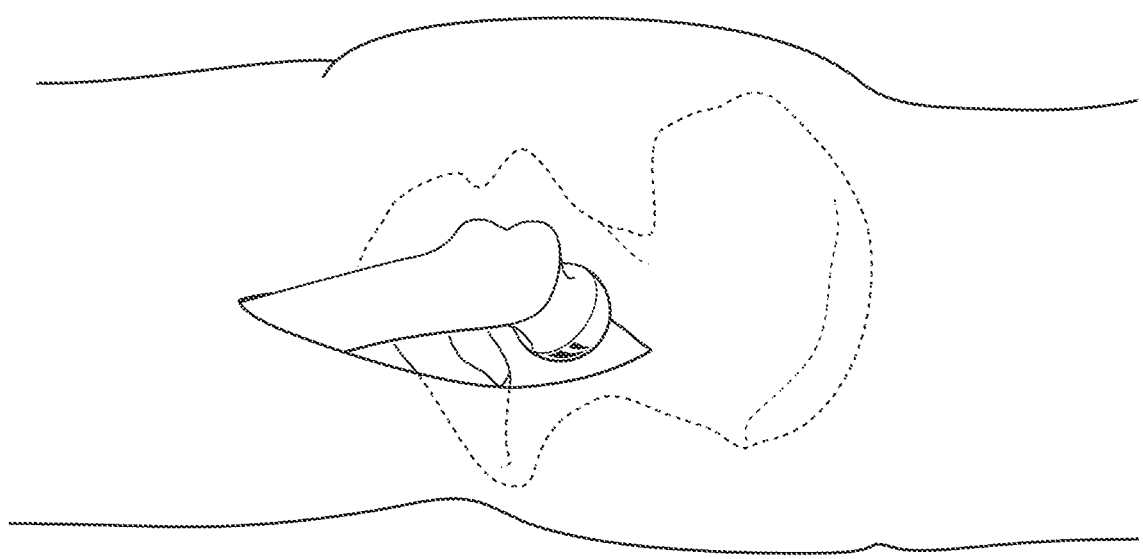
FIG. 3 shows the step of removing the caput femur from the hip joint capsule.

FIG. 3 shows the placing of an artificial caput femur surface 45 on the caput femur 5 in conventional surgery. However according to other embodiments of the state of the art the entire collum femur 6 is removed using a bone saw, after which a prosthetic part comprising the caput femur is fixated in the femoral bone using bone cement or mechanical fixating members. A bowl shaped cup is then placed in the acetabulum 8 to act as the contacting surface against the new artificial caput femur 45 when the hip joint is performing functional hip movements in its functional position. According to prior art, the artificial caput femur surface and the artificial acetabulum surface is being kept together by means of the hip joint capsule, which is dramatically weakened when the capsule has been penetrated during an operation.

An alternative way of operating a hip joint will now be described.

Figure 4:
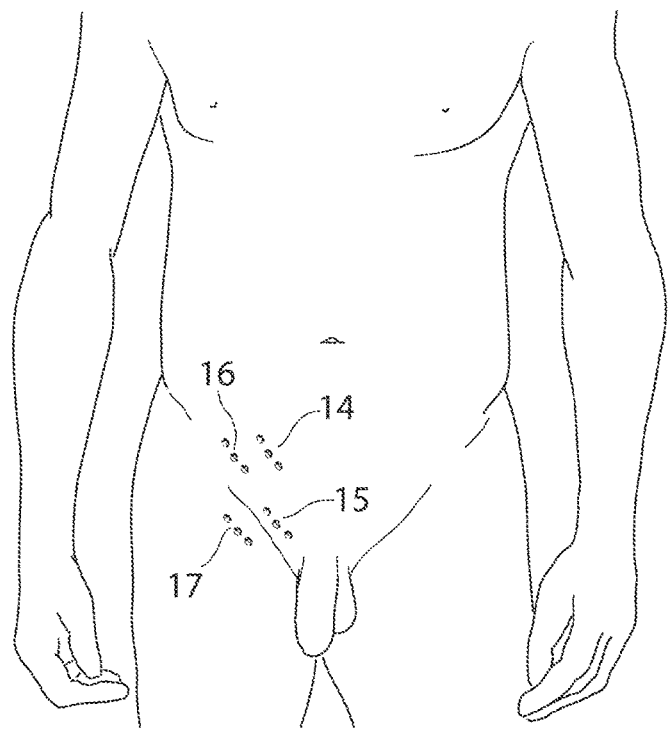
FIG. 4 shows the incisions made in a laparoscopic/arthroscopic method.

FIG. 4 shows a frontal view of the body of a human patient. A laparoscopic/arthroscopic method of operating the hip joint, from the opposite side from acetabulum, is according to a first embodiment performed starting with making small incisions 14 in the abdominal wall of the human patient. The small incisions enable the surgeon to insert laparoscopic trocars into the abdomen of the human patient. According to the first embodiment the incisions 14 passes through the rectus abdominis and peritoneum in to the abdomen of the human patent. According to a second preferred embodiment the small incisions 15 is conducted through the rectus abdominis and in to the pelvic area, below peritoneum. According to a third embodiment the small incisions 16 is performed just between Ilium and the surrounding tissue, an incision 16 which could enable the pelvic bone to be dissected with very little penetration of fascia and muscular tissue. According to a fourth embodiment the incision 17 is made in the inguinal channel. In all of the four embodiments the tissue surrounding the pelvic bone 9 in the area opposite to acetabulum 8 is removed or penetrated which enables the surgeon to reach the pelvic bone 9.

It is obvious that the methods described may both be combined or altered reaching the same goal to dissect the pelvic bone on the opposite side of the acetabulum.

Figure 6:
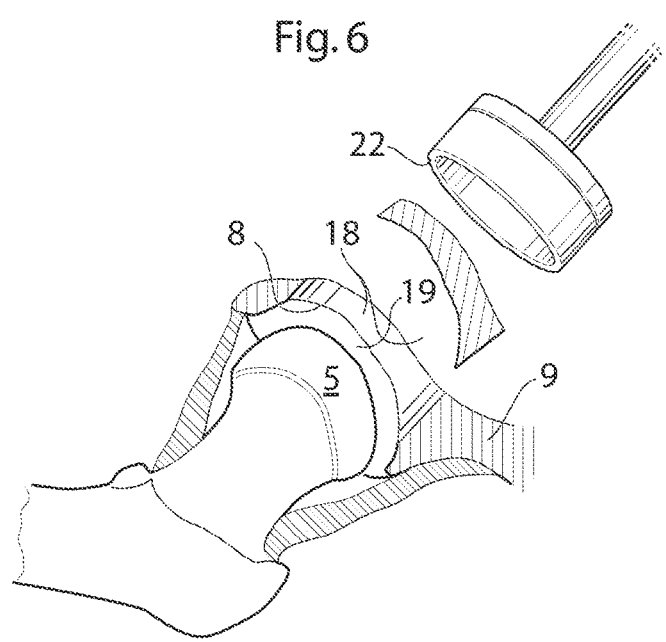
FIG. 6 shows the step of creating a hole in the pelvic bone of a patient.

After dissecting the pelvic bone 9 a hole 18 is created in the bone 9, as shown in FIG. 6. The hole 18 passes through the pelvic bone from the opposite side from acetabulum 8 and into the hip joint 19.

Figure 5:
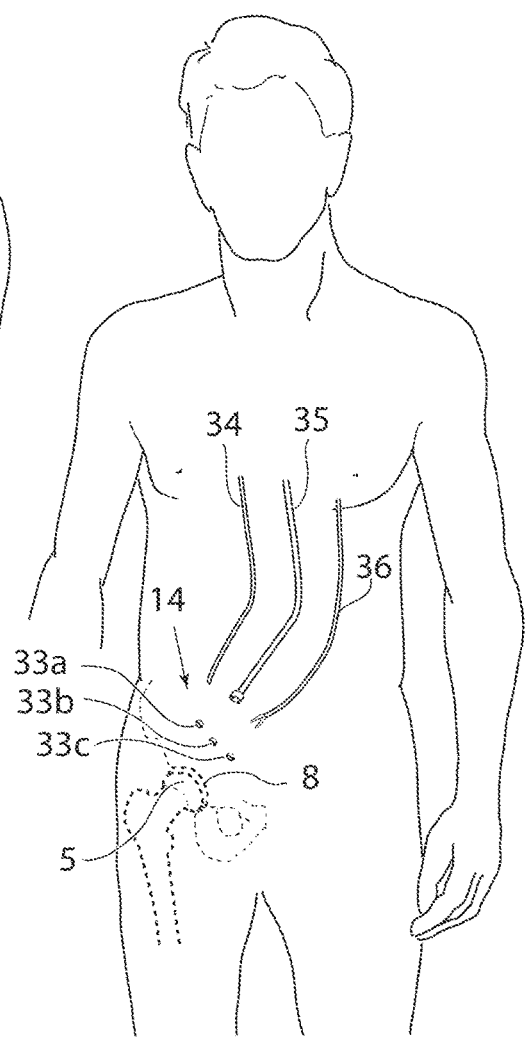
FIG. 5 shows the instruments used in a laparoscopic/arthroscopic method.

FIG. 5 shows a frontal view of the body of a human patient, illustrating the laparoscopic method of operating the hip joint from the opposite side from acetabulum 8. The hip joint comprises the acetabulum 8 and the caput femur 5. The small incisions 14 in the abdominal wall of the human patient allows the insertion of laparoscopic trocars 33a,b,c into the body of the patients. Whereafter one or more camera 34, a surgical instrument adapted to create a hole in the pelvic bone 35, or instruments 36 for introducing, placing, connecting, attaching, creating or filling prosthesis or prosthetic parts, can be inserted into said body through said laparoscopic trocars 33a,b,c.

Figure 7:
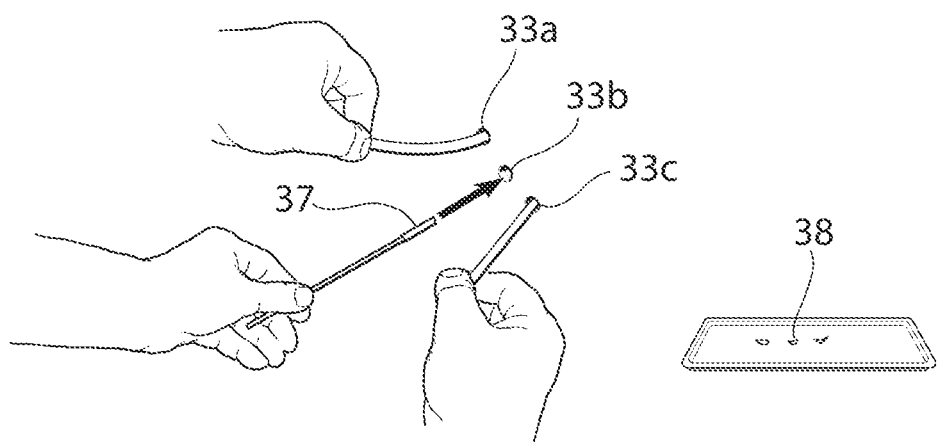
FIG. 7 shows details of a laparoscopic operation.

FIG. 7 shows a close-up of the insertion 37 of prosthetic parts 38 into the patient's body through said laparoscopic trocars 33a,b,c. The prosthetic parts could be parts of the artificial caput femur 45, the artificial acetabulum 65 or prosthetic parts or bone material adapted to be used to close the hole 18 created in the pelvic bone 9.

Figure 8:
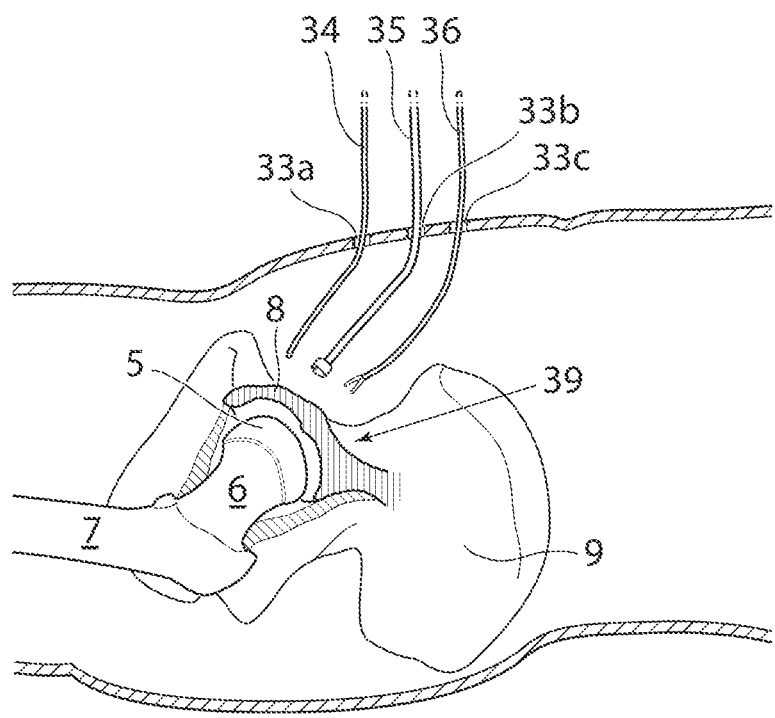
FIG. 8 shows the patient in section when a laparoscopic operation is performed.

FIG. 8 shows a lateral view of the body of a human patient, with the hip joint shown in section. The hip joint comprises a caput femur 5 placed at the very top of collum femur 6 which is the top part of the femur bone 7. The caput femur 5 is in connection with the acetabulum 8 which is a bowl shaped part of the pelvic bone 9. Laparoscopic trocars 33a,b,c is being used to reach the hip joint 39 with one or more camera 34, a surgical instrument 35 adapted to create a hole in the pelvic bone 9, or instruments 36 for introducing, placing, connecting, attaching, creating or filling prosthesis or prosthetic parts.

Figure 9:
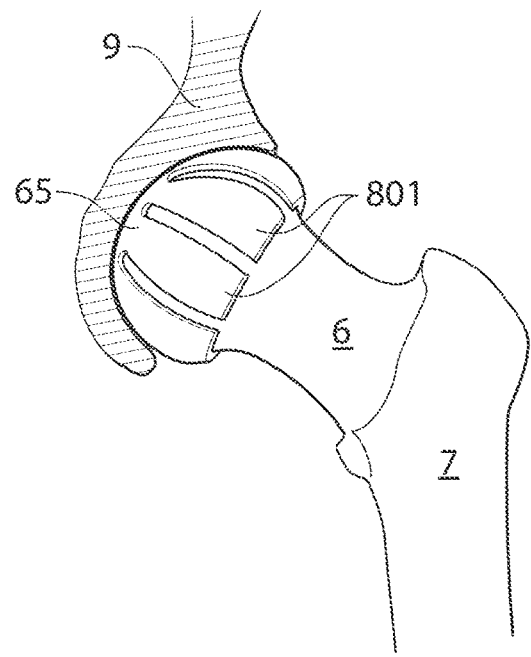
FIG. 9 shows the hip joint in section when a medical device has been provided, in a first state.

FIG. 9 shows an artificial bowl shaped acetabulum cup 65 placed in the pelvic bone 9. The artificial bowl shaped acetabulum cup 65 comprises releasing members 801 adapted, in a first state, to hold the caput femur 5 which is a ball shaped piece attached to the collum femur 6 in position in the hip joint to the artificial bowl shaped acetabulum cup 65 placed in the pelvic bone 9. In a second state the releasing member 801 is adapted to release the caput femur 5, or an artificial replacement therefore, from the artificial bowl shaped acetabulum cup 65 placed in the pelvic bone 9. The releasing member 801 is adapted to change from the first state to the second state when a pre-determined strain is placed on the releasing member 801. The strain preferably being caused by an abnormal movement of the hip joint, e.g. as the result of the patient falling. According to the embodiment shown in FIG. 9 the releasing member 801 comprises an elastic portion comprising elastic material, in the embodiment shown being the entire releasing member 801. The releasing member is adapted to non-invasively be able to change from the first state to the second state and from the second state to the first state, when a pre-determined strain is placed on the releasing member 801.

Figure 10:
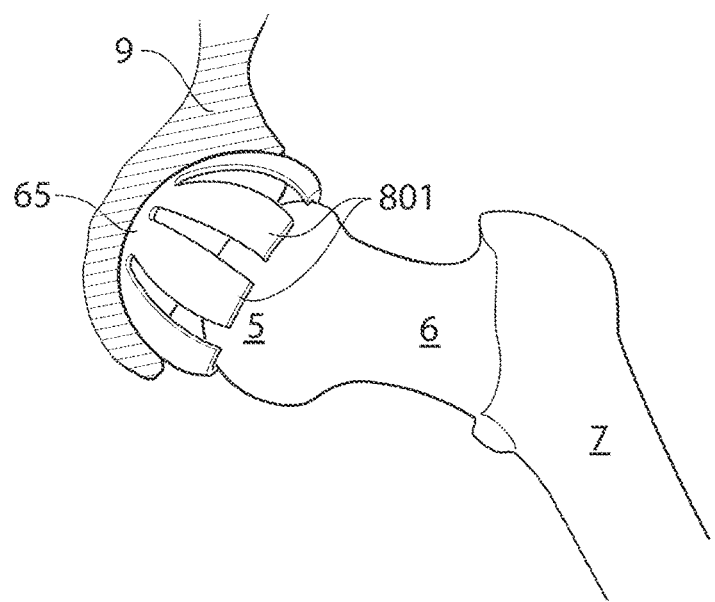
FIG. 10 shows the hip joint in section when a medical device has been provided, in a second state.

FIG. 10 shows the hip joint in section when the releasing member 801 is in its second state, wherein the releasing member 801 is adapted to release the caput femur 5, or an artificial replacement therefore, from the artificial bowl shaped acetabulum cup 65 placed in the pelvic bone 9. The releasing member 801 has changed from the first state to the second state because of a pre-determined strain has been placed on the releasing members 801.

Figure 11:
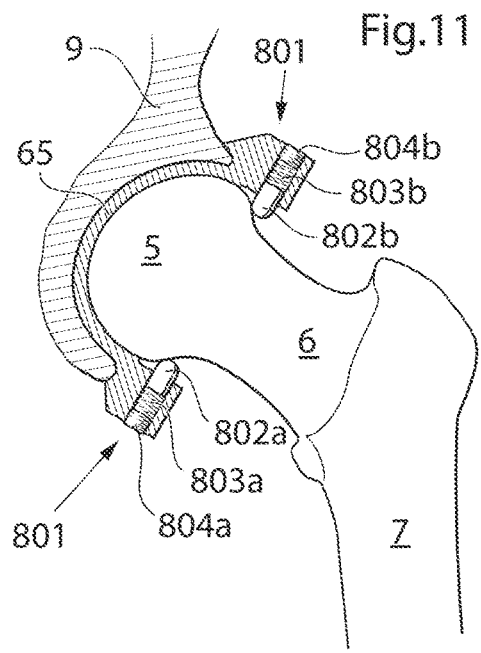
FIG. 11 shows the hip joint in section when a medical device has been provided, in a first state.

FIG. 11 shows the medical device according to an embodiment where the artificial bowl shaped acetabulum surface 65 comprises releasing members 801 comprising holding members 802a,b adapted to slide against the caput femur 5, or an artificial replacement therefore. The holding members are adapted to, in a first state, hold the caput femur 5, or an artificial replacement therefore, which is a ball shaped part attached to the collum femur 6 in position in the hip joint to the artificial bowl shaped acetabulum cup 65 placed in the pelvic bone 9. In a second state the releasing member 801 is adapted to release the caput femur 5, or an artificial replacement therefore, from the artificial bowl shaped acetabulum cup 65 placed in the pelvic bone 9. The holding members 802a,b are spring loaded through a spring 803a,b being placed between a calibration member, being a calibration screw 804a,b, and the holding members 802a,b. The force exerted on the holding members 802a,b from the spring 803a,b is adapted to hold the caput femur 5, or an artificial replacement therefore, in the artificial acetabulum 65 in normal, functional hip joint movements, but release the caput femur 5, or an artificial replacement therefore, from the artificial acetabulum 65 when a pre-determined strain is placed on the releasing member preferably being caused by an abnormal movement of the hip joint, e.g. as the result of the patient falling. The calibration screws 804a,b enables the pre-determination of the strain which will cause the holding members 802a,b to change from being in a first state to being in a second state.

Figure 12:
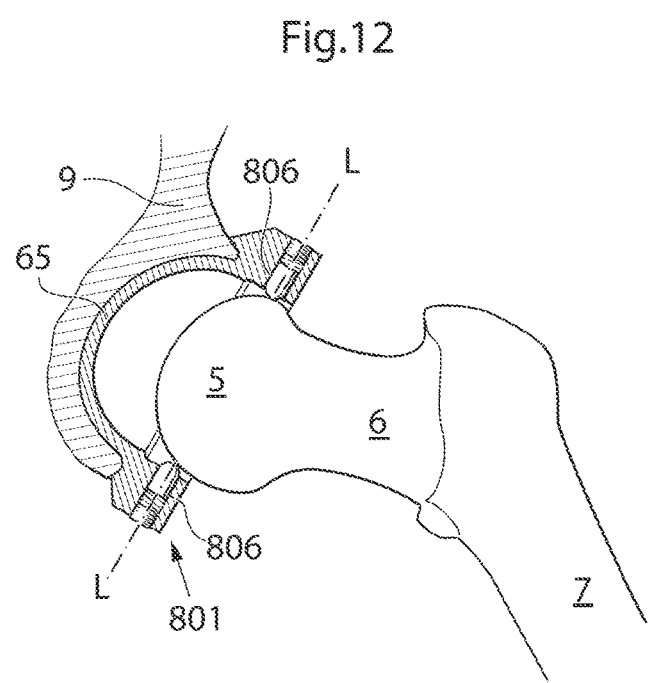
FIG. 12 shows the hip joint in section when a medical device has been provided, in a second state.

FIG. 12 shows the releasing members in their second state, when a pre-determined strain has been exceeded, preferably being caused by an abnormal movement of the hip joint, e.g. as the result of the patient falling. The holding members 802a,b are retracted into sleeves 806 of the artificial acetabulum surface 65, thereby compressing the springs 803a,b. The retraction of the holding members 802a,b causes the caput femur 5, or an artificial replacement therefore, to be dislocated/luxated from its position in the artificial acetabulum surface 65, which, when large strain is placed on the hip joint and femoral bone 7, reduces the risk of the patient fracturing the femoral bone 7 or the pelvic bone 9. The holding members 802a,b are adapted to non-invasively be able to change from the first state to the second state and from the second state to the first state, when a pre-determined strain is placed on the holding members 802a,b.

Figure 13:
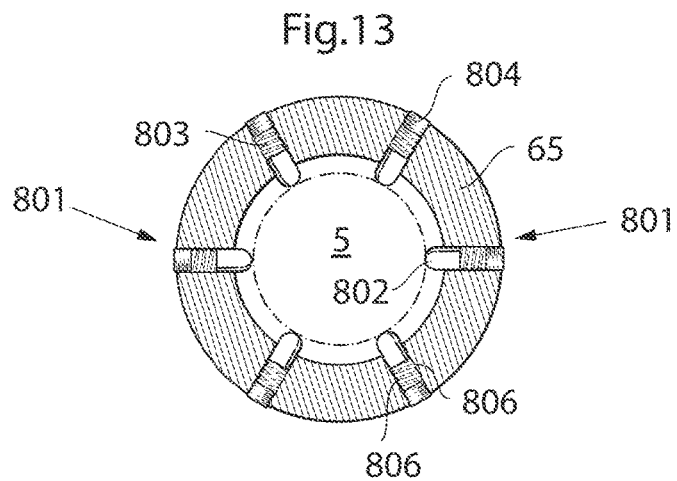
FIG. 13 shows the medical device in section.

FIG. 13 shows the artificial acetabulum 65 in section with the holding members 802, placed in sleeves 806 evenly distributed along the cross-section of the artificial acetabulum 65, holding the caput femur 5, or an artificial replacement therefore, in position in the artificial acetabulum 65.

Figure 14:
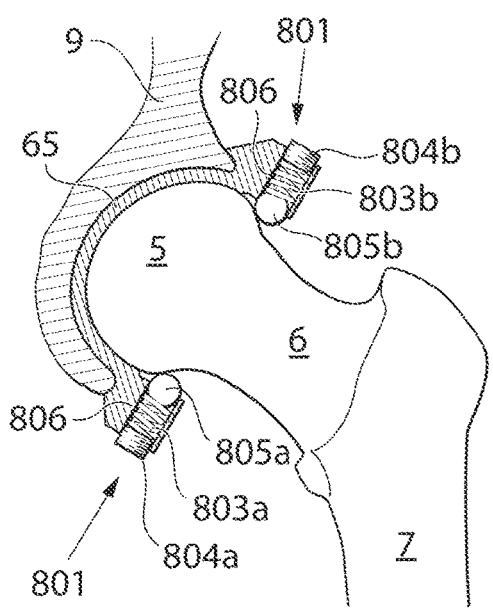
FIG. 14 shows an alternative embodiment of the medical device shown in FIG. 11, in a first state.

FIG. 14 shows an alternative embodiment of the principle shown in FIGS. 11-13, wherein the holding members 802a, b, comprises ball shaped members 805a,b in contact with the caput femur 5, or an artificial replacement therefore, ant being adapted to roll against the caput femur 5, or an artificial replacement therefore, holding the caput femur 5, or an artificial replacement therefore, in place in the artificial acetabulum 65 by the holding members 802a,b exerting force on the caput femur 5, or an artificial replacement therefore, through the contact with the springs 803a,b supported by the calibration screws 804a,b.

Figure 15:
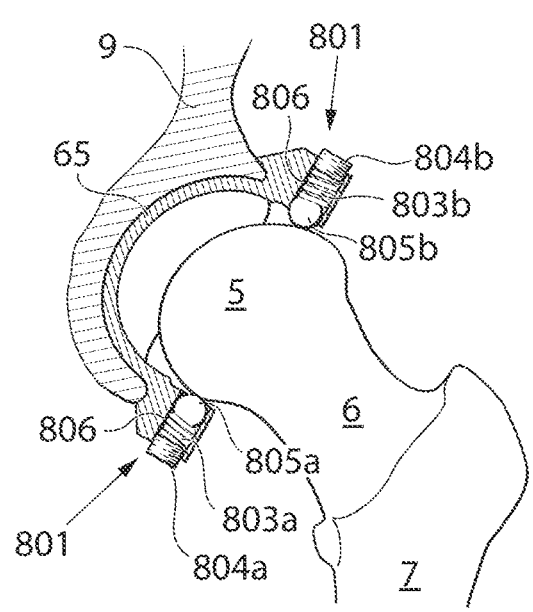
FIG. 15 shows an alternative embodiment of the medical device shown in FIG. 11, in a second state.

FIG. 15 shows the releasing members in their second state, when a pre-determined strain has been exceeded, preferably being caused by an abnormal movement of the hip joint, e.g. as the result of the patient falling. The holding members 802a,b, comprising the ball shaped members 805a, b, are retracted into sleeves 806 of the artificial acetabulum surface 65, thereby compressing the springs 803a,b. The retraction of the holding members 802a,b causes the caput femur 5, or an artificial replacement therefore, to be dislocated/luxated from its position in the artificial acetabulum surface 65, which, when large strain is placed on the hip joint and femoral bone 7, reduces the risk of the patient fracturing the femoral bone 7 or the pelvic bone 9. The holding members 802a,b are adapted to non-invasively be able to change from the first state to the second state and from the second state to the first state, when a pre-determined strain is placed on the holding members 802a,b, which enables the caput femur 5, or an artificial replacement therefore, to be replaced in the artificial acetabulum 65 without a surgical procedure.

Figure 16:
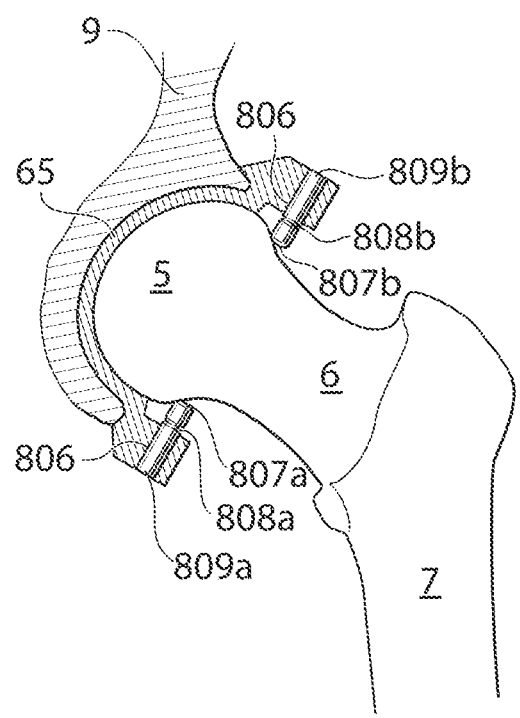
FIG. 16 shows the hip joint in section, when a medical device according to yet another embodiment is provided, in a first state.

FIG. 16 shows the medical device in an embodiment wherein the releasing members 801 comprises a rupture device 807, 808, 809 adapted to fail at a pre-determined strain. According to this embodiment the rupture device is a rupture pin 807, 808, 809 comprising a base part 809a,b fixated to the artificial acetabulum 65 and a rupture part 807a,b attached to the base part 809a,b through a weakened section 808a,b, in which section the rupture part 807a,b is detached from the base part 809a,b when a predetermined strain is placed on the rupture device in contact with the caput femur 5, or an artificial replacement therefore.

Figure 17:
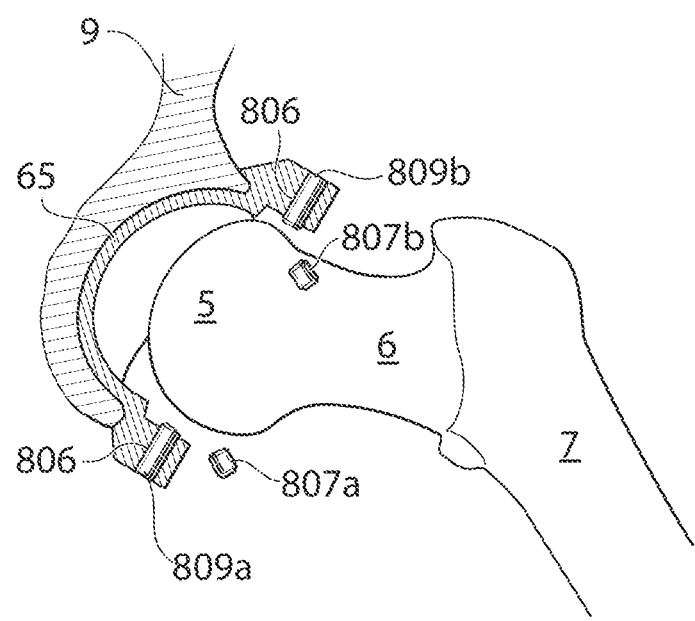
FIG. 17 shows the hip joint in section, when a medical device according to yet another embodiment is provided, in a second state.

FIG. 17 shows the medical device according to the embodiment of FIG. 16 when the rupture device has failed due to a pre-determined strain on the rupture device being exceeded. According to one embodiment, (not shown) the rupture parts 807a,b are secured to the base part through a security wire keeping rupture parts 807a,b in proximity to the base part 809a,b even after the failure of the rupture device.

Figure 18A:
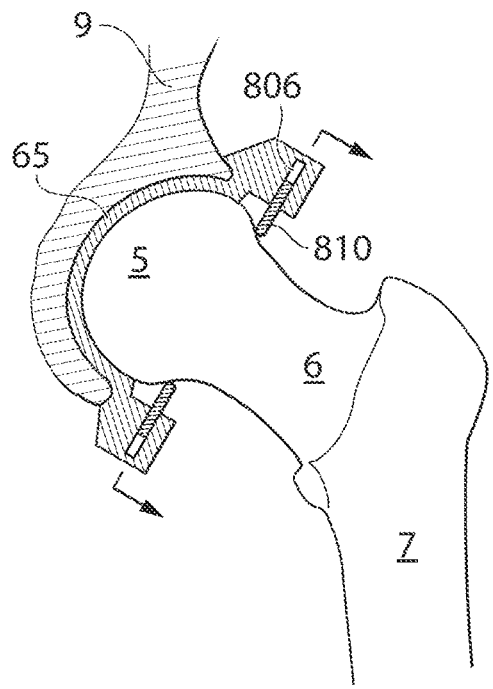
FIG. 18a shows the hip joint in section when a medical device comprising an elastic or rupture band has been provided, in a first state.

FIG. 18a shows the medical device according to an embodiment where the artificial acetabulum 65 comprises a circular sleeve 806, in which an elastic or rupture band 810 is provided. The elastic or rupture band 810 is adapted to at least partly encircle the ball shaped caput femur 5, or artificial replacement therefore. When a pre-determined strain is placed on the elastic or rupture band 810 the circular opening encircling the caput femur 5, or an artificial replacement therefore, is expanded and the caput femur 5, or an artificial replacement therefore, is released from the artificial acetabulum 65, to which it is held by means of the elastic band 610. In embodiments where the medical device comprises a rupture band 810 holding the caput femur 5, or an artificial replacement therefore, in the artificial acetabulum 65, a weakened portion 811 of the band 810 fails and thus the circular opening encircling the caput femur 5, or an artificial replacement therefore, is expanded and the caput femur 5, or an artificial replacement therefore, is released from the artificial acetabulum 65. In the embodiments where the band 810 is an elastic band 810 it is conceivable that the band 810 comprises an elastic part or section, or that the entire band 810 is made of an elastic material.

Figure 18B:
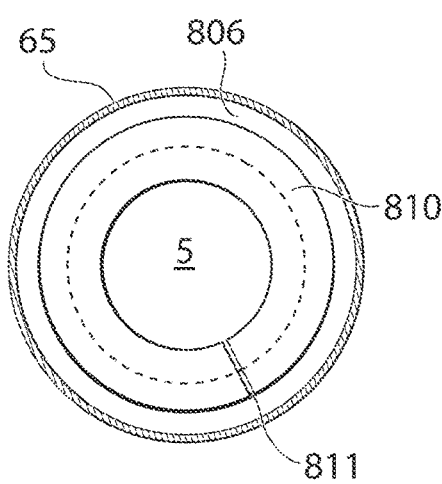
FIG. 18b shows the medical device of FIG. 18a, in section, in a first state.

FIG. 18b shows the medical device in section when the elastic or rupturing band 810, holding the caput femur 5, or an artificial replacement therefore, is placed in a circular sleeve 806 in the artificial acetabulum 65. An opening or weakened portion 811 is provided perpendicular to the circumference of the band 810.

Figure 19A:
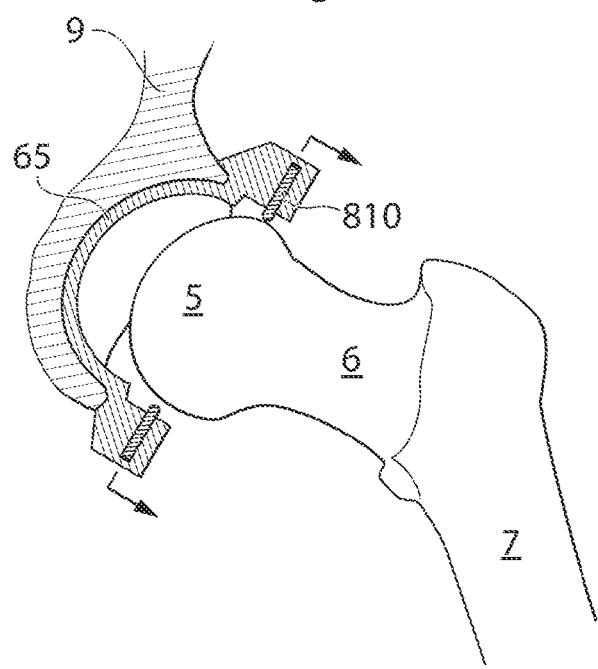
FIG. 19a shows the hip joint in section when a medical device comprising an elastic or rupture band is provided, in a second state.
Figure 19B:
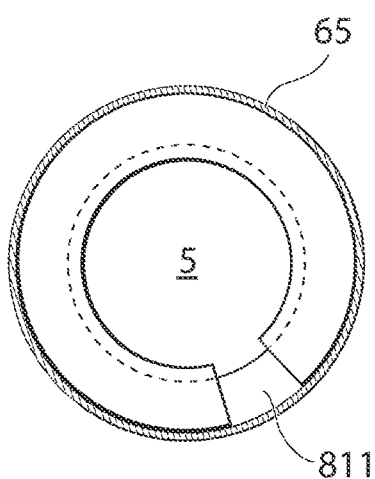
FIG. 19b shows the medical device of FIG. 19a, in section, in a second state.

FIG. 19a shows the medical device in a second state where the caput femur 5, or an artificial replacement therefore, is released from the connection with the acetabulum, after a pre-determined stain has been placed on the elastic or rupture band 810. As shown in FIG. 19b the gap or weakened part has been expanded, thereby allowing the caput femur, or an artificial replacement therefore, 5 to pass through the opening defined by the elastic or rupture band 810. The medical device could be adapted to non-invasively be able to change from the first state to the second state and from the second state to the first state, when a pre-determined strain is placed on the band 810, which enables the caput femur 5, or an artificial replacement therefore, to be replaced in the artificial acetabulum 65 without a surgical procedure.

Figure 20:
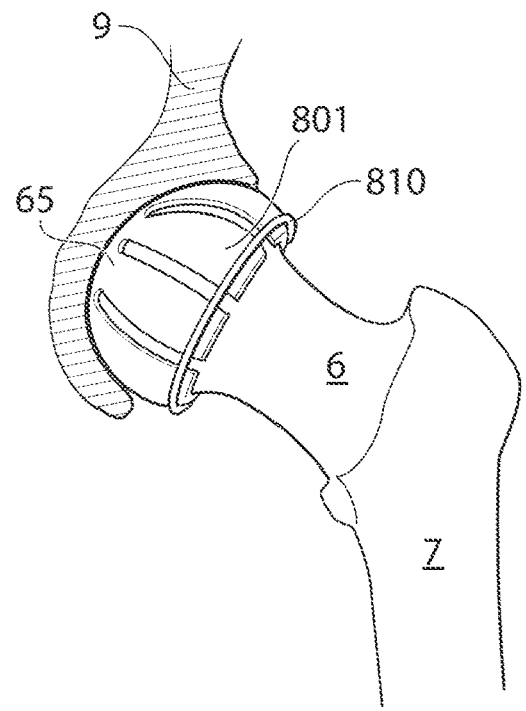
FIG. 20 shows the hip joint in section, when a medical device according to yet another embodiment has been provided, in a first state.

FIG. 20 shows the medical device according to an embodiment where the releasing member 801 comprises an elastic wing of the artificial acetabulum 65, which is assisted by an elastic or rupture band 810 encircling the medical device by enclosing the caput femur 5, or an artificial replacement therefore, in the artificial acetabulum 65 passing beyond the point of the caput femur 5, or an artificial replacement therefore, having a largest cross-sectional distance. The elastic or rupture band 810 is held in place to the artificial acetabulum 65 by means of the band 810 being placed in a groove along the circumference of the artificial acetabulum 65. However, said groove could be assisted or replaced by an adhesive or a mechanical fixation element.

Figure 21:
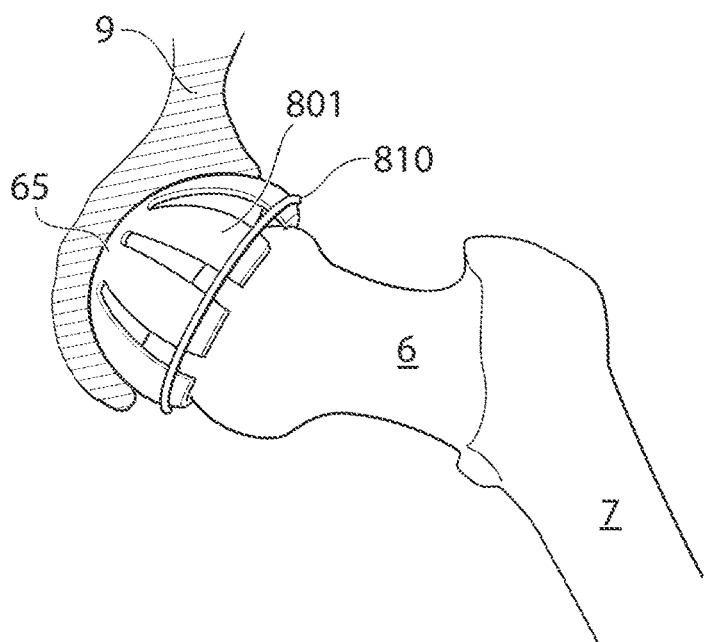
FIG. 21 shows the hip joint in section, when a medical device according to yet another embodiment has been provided, in a second state.

FIG. 21 shows the medical device when in its second state, in which the releasing member 801 releases the caput femur 5, or an artificial replacement therefore, from the artificial acetabulum 65. In embodiments when the band 810 is an elastic band 810 it is expanded, thereby enlarging the hole through which the caput femur 5, or an artificial replacement therefore, can pass. In embodiment where the band 810 is a rupture band, the band 810 has failed and thereby the caput femur 5, or an artificial replacement therefore, is held in place solely by the releasing member 801 which is adapted to release the caput femur 5, or an artificial replacement therefore, at a pre-defined strain. The medical device could be adapted to non-invasively be able to change from the first state to the second state and from the second state to the first state, when a pre-determined strain is placed on the band 810 and/or the releasing member 801, which enables the caput femur 5, or an artificial replacement therefore, to be replaced in the artificial acetabulum 65 without a surgical procedure.

Figure 22:
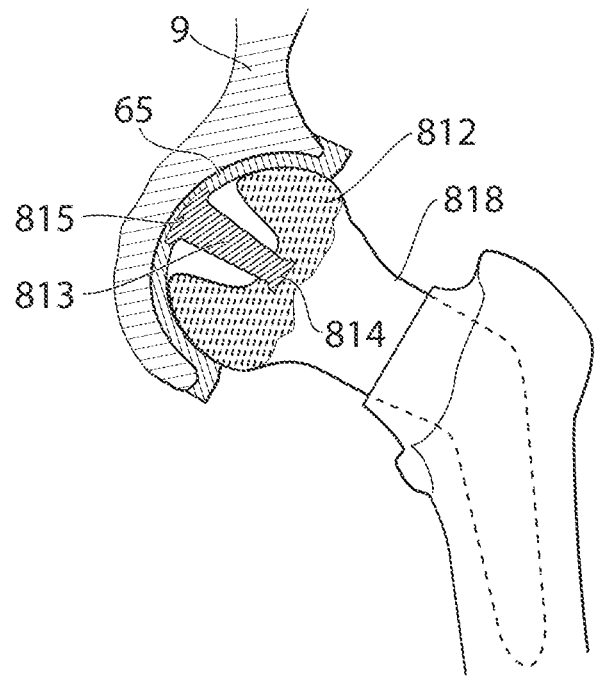
FIG. 22 shows the hip joint in section, when a medical device comprising a rupture band has been provided, in a first state.

FIG. 22 shows the hip joint in section according to an embodiment where the caput femur 5, or an artificial replacement therefore, and collum femur 6 have been replaced with a prosthetic part 818 fixated to the femoral bone 7, either with bone cement, or without. The prosthetic part 818 comprises an artificial caput femur 812 having a cavity 816 in which a rupture band 813 fixated to a fixation portion 814 of the artificial caput femur 812, and a fixating portion 815 of the artificial acetabulum 65. The cavity 816 is adapted to enable the artificial caput femur 812 to perform normal functional hip movements inside the artificial acetabulum 65. The rupture band 813 is adapted to hold the artificial caput femur 812 to the artificial acetabulum 65 in a first state, and release the artificial caput femur 812 from the artificial acetabulum when a pre-determined strain is placed on the rupture band 813.

Figure 23:
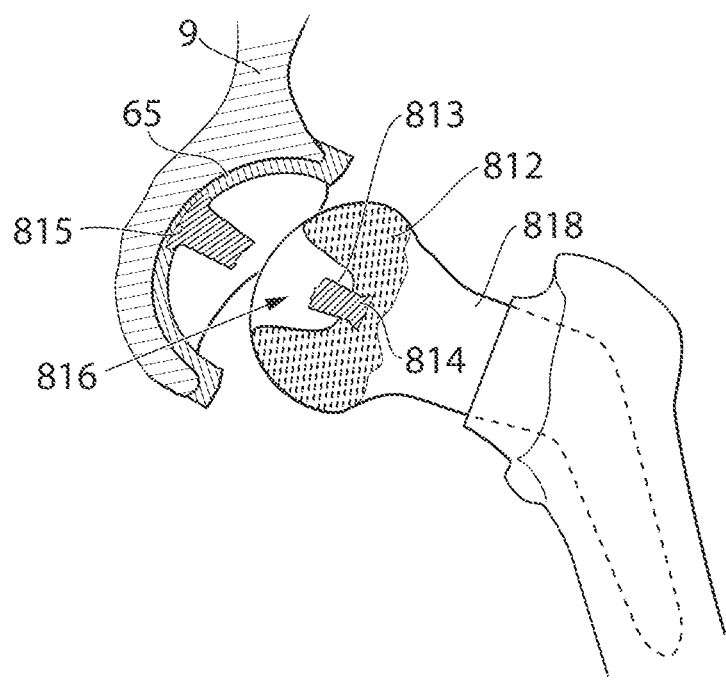
FIG. 23 shows the hip joint in section, when a medical device comprising a rupture band has been provided, in a second state.

FIG. 23 shows the embodiment of the medical device according to FIG. 22, in a second state in which the rupture band 813 has failed and thereby the artificial caput femur 812 is released from the artificial acetabulum 65. The rupture band 813 could be fixated to a fixation portion 814 of the artificial caput femur 812, and/or a fixating portion 815 of the artificial acetabulum 65 using: at least one screw, at least one pin, form fitting, welding, adhesive, pin, wire, a ball mounted into a bowl, a male portion of one part mounted into a female portion of the other part, a key introduced into a lock being portions of said parts, band, or other mechanical connecting members. The failing of the rupture band 813 is preferably caused by an abnormal movement of the hip joint, e.g. as the result of the patient falling.

Figure 24:
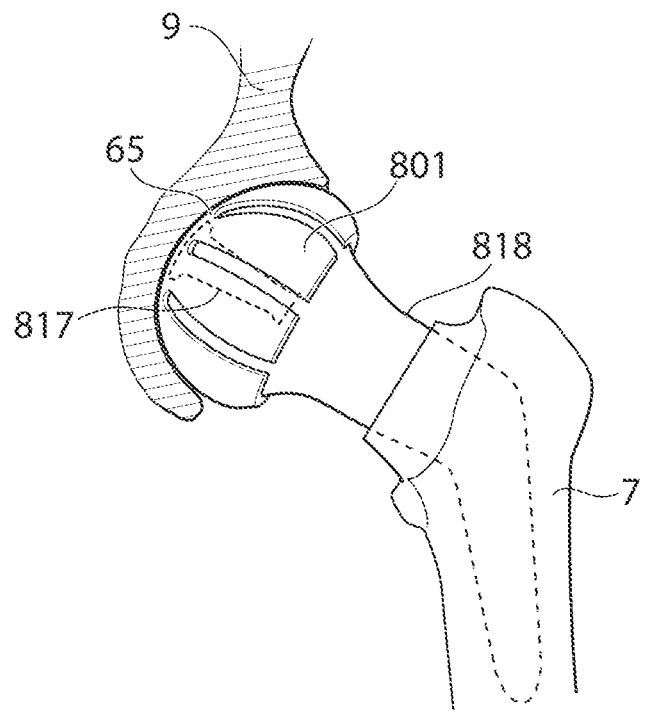
FIG. 24 shows the hip joint in section, when a medical device according to yet another embodiment has been provided, in a first state.

FIG. 24 shows a prosthetic part 818 according to an embodiment where the prosthetic part 818 is fixated to the femoral bone 7 and comprises a caput femur 812 comprising a cavity 816 adapted to enable the hip joint to perform functional hip joint movements while in a first state held to the artificial acetabulum using an elastic bend 817 fixated to a fixation portion 814 of the artificial caput femur 812, and a fixating portion 815 of the artificial acetabulum 65, and a releasing member 801 according to the embodiment shown in FIGS. 9 and 10. The combination of the releasing member 801 and the elastic band 817 is adapted to, in a first state hold the prosthetic part 818 to the artificial acetabulum 65, and in a second state release the prosthetic part 818 from the artificial acetabulum 65. According to another embodiment (not shown) the prosthetic part is held to the artificial acetabulum 65 solely using the elastic band 817, of course also supported by the remainder of the hip joint capsule and the affected muscles.

Figure 25:
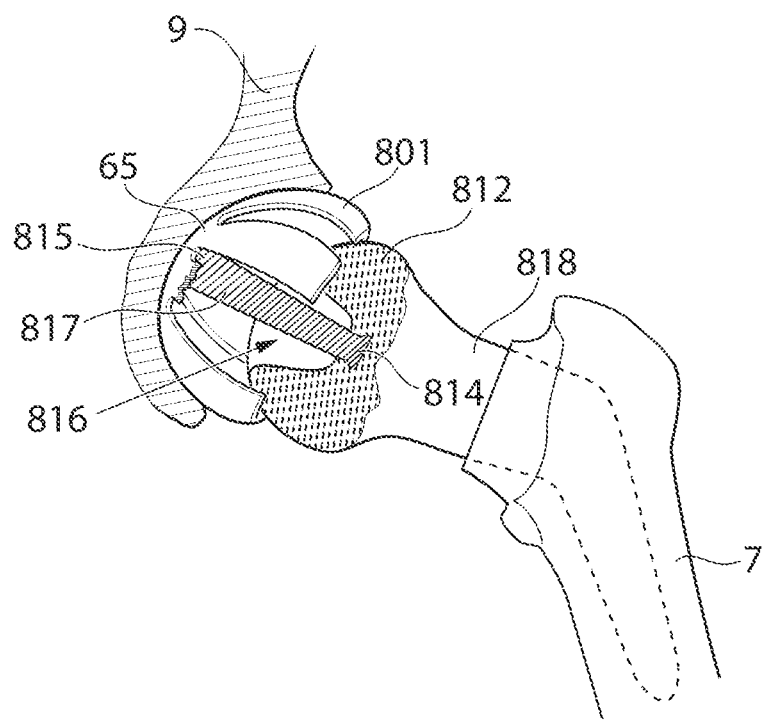
FIG. 25 shows the hip joint in section, when a medical device according to yet another embodiment has been provided, in a second state.

FIG. 25 shows the embodiment of the medical device according to FIG. 24, in a second state in which the elastic band 817 is stretched such that the prosthetic part 818 is released from the artificial acetabulum artificial acetabulum 65. The elastic band 817 could be fixated to a fixation portion 814 of the artificial caput femur 812, and/or a fixating portion 815 of the artificial acetabulum 65 using: at least one screw, at least one pin, form fitting, welding, adhesive, pin, wire, a ball mounted into a bowl, a male portion of one part mounted into a female portion of the other part, a key introduced into a lock being portions of said parts, band, or other mechanical connecting members. The failing of the rupture band 813 is preferably caused by an abnormal movement of the hip joint, e.g. as the result of the patient falling. Preferably the elastic band 817 comprises an elastic part or section, which could be the entire elastic band 818, made from an elastic material, such as an elastic polymer material such as: a copolymer material such as polystyrene, poly(ethylene-butylene) or polystyrene. It is also conceivable that the material is a polyurethane elastomeric material, polyamide elastomeric materials and polyester elastomeric materials elastic copolymers of ethylene and at least one vinyl monomer such as, for example, vinyl acetates, unsaturated aliphatic monocarboxylic acids, and esters of such monocarboxylic acids. The elastic band 813 could comprise a barrier coating, which cannot be penetrated by body cells. Preferably, the barrier coating comprises a Parylene™ coating, or a biocompatible metal coating, such as gold, silver or titanium. According to other embodiments the elastic band comprises a spring type member, a combination of metal and plastic materials, a combination of metal and carbon based material or a combination of carbon and plastic based material.

Figure 26:
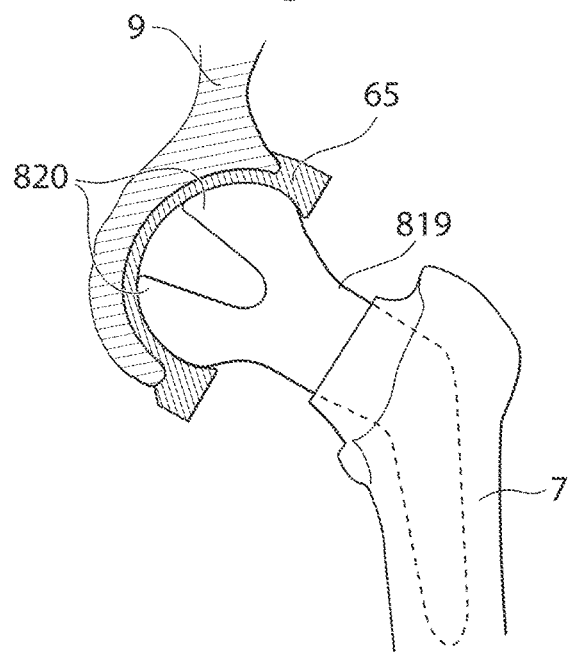
FIG. 26 shows the hip joint in section when a medical device, according to an embodiment where the artificial acetabulum surface comprises elastic elements, has been provided, in a first state.

FIG. 26 shows the hip joint in section in an embodiment where the medical device comprises a prosthetic part 819 adapted to be fixated to the femoral bone 7. The prosthetic part comprises an artificial caput femur which is adapted to comprise elastic elements 820 which act as a releasing member holding the artificial caput femur inside of the artificial acetabulum 65 fixated to the pelvic bone. The elastic elements 820 of the artificial caput femur, is preferably made of an elastic material, which for example could be an elastomeric polymer material or an elastic metal material. It is conceivable that the elastic material comprises an outer layer in connection with the artificial acetabulum 65 which is adapted to resist the wear from the contact with the artificial acetabulum surface. The elastic element is adapted to compress when a pre-determined strain is placed on the hip joint and thereby on the elastic elements 820. When the elastic elements 820 are compressed the artificial caput femur is released from the artificial acetabulum 65.

Figure 27:
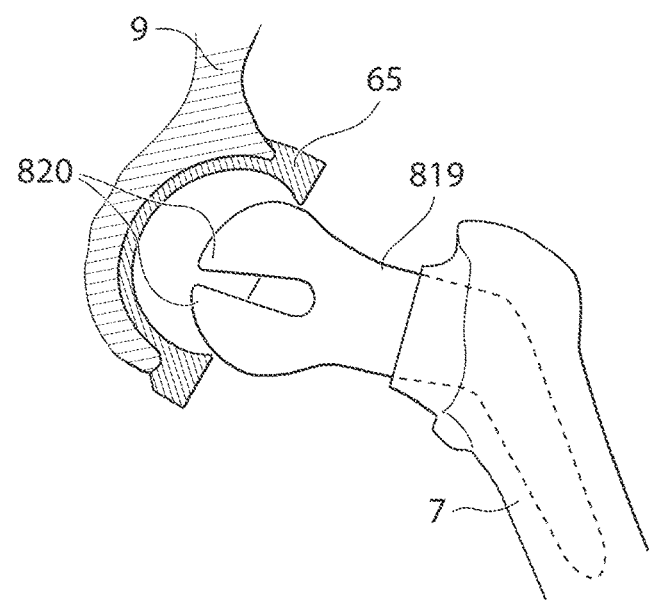
FIG. 27 shows the hip joint in section when a medical device, according to an embodiment where the artificial acetabulum surface comprises elastic elements, has been provided, in a second state.

FIG. 27 shows the medical device according to the embodiment shown in FIG. 27, in a second state, in which the elastic element 820 has been compressed, following a pre-determined strain being placed on the medical device. The medical device is thereby placed in a second state, in which the artificial caput femur is released from the artificial acetabulum 65, wherein it has been held.

Figure 28:
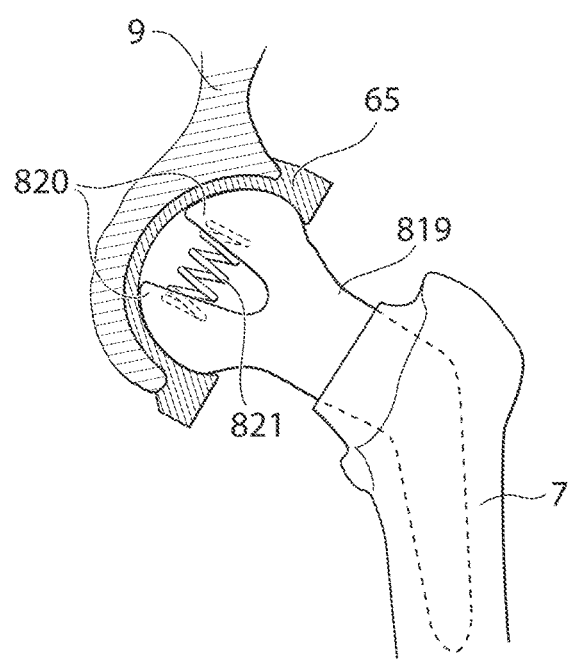
FIG. 28 shows an alternative embodiment of the medical device shown in FIG. 26.

FIG. 28 shows an embodiment of the medical device in which the elastic elements 820 are further assisted by a spring 821 in connection with two elastic elements 820, the spring 821 is compressed alongside the elastic members 820, when a pre-determined strain is placed on the prosthetic part 819 comprising the artificial caput femur.

Figure 29:
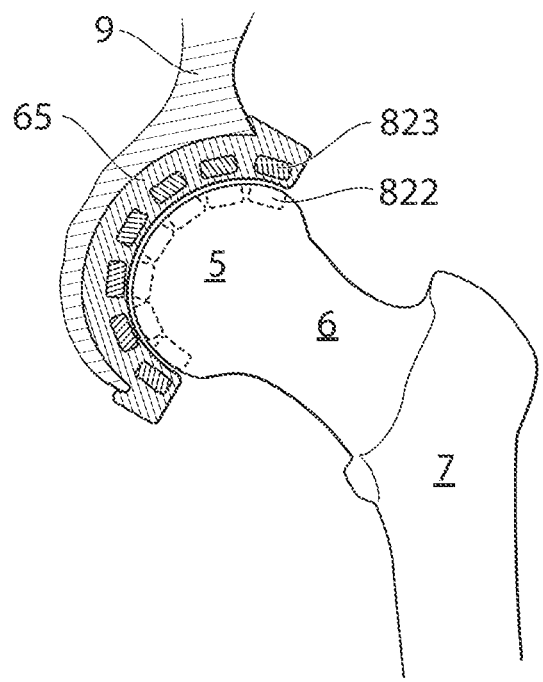
FIG. 29 shows the hip joint in section when a medical device adapted to hold the caput femur 5, or an artificial replacement therefore, to the artificial acetabulum by means of magnetic force, has been provided, in a first state.

FIG. 29 shows the hip joint in section when a medical device for, in a first state, holding the caput femur 5, or an artificial replacement therefore, to the artificial acetabulum 65, and in a second state releasing the caput femur 5, or an artificial replacement therefore from the artificial acetabulum 65. The medical device is adapted to change from being in the first state to being in the second state at a pre-determined strain affecting the medical device by the connection with the pelvic bone 9 and the femoral bone 7, which reduced the risk of the patient fracturing the femoral bone 7 and/or the pelvic bone 9. The medical device comprises magnets 823 or magnetic material 823 placed in the artificial acetabulum 65, and magnets 822 or magnetic material 822 placed in the caput femur 5 or an artificial replacement therefore. According to one embodiment a magnet 823 is placed in the artificial acetabulum having its south pole directed towards the caput femur 5, or artificial replacement therefore, and a magnet 822 placed in the caput femur 5, or artificial replacement therefore, having its north pole directed towards the artificial acetabulum 65. However it is easily understood by the skilled in the art that only one of the sides needs to be magnetic whereas the other side merely needs to comprise magnetic material. Any combination of north and south ends and magnets/magnetic material is hence conceivable. The magnetic force described is adapted to hold the caput femur 5, or an artificial replacement therefore, in the acetabulum in normal use, enabling the hip joint to perform functional hip joint movements, and release the caput femur 5, or an artificial replacement therefore, from the artificial acetabulum 65 when a predetermined strain is exceeded.

Figure 30:
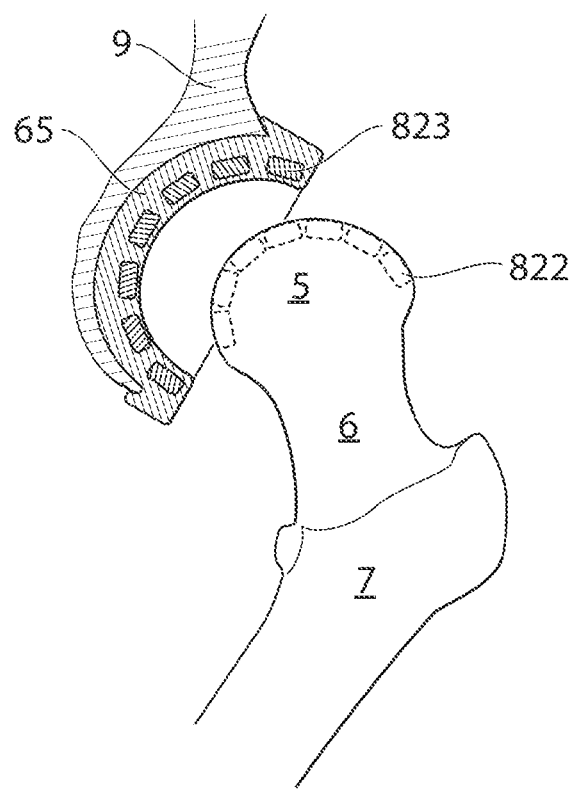
FIG. 30 shows the hip joint in section when a medical device adapted to hold the caput femur 5, or an artificial replacement therefore, to the artificial acetabulum by means of magnetic force, has been provided, in a second state.

FIG. 30 shows the medical device according to the embodiment of FIG. 30 in the second state, in which the caput femur 5, or an artificial replacement therefore, is released from the artificial acetabulum 65 as a result of a pre-determined level of strain being exceeded.

Figure 31:
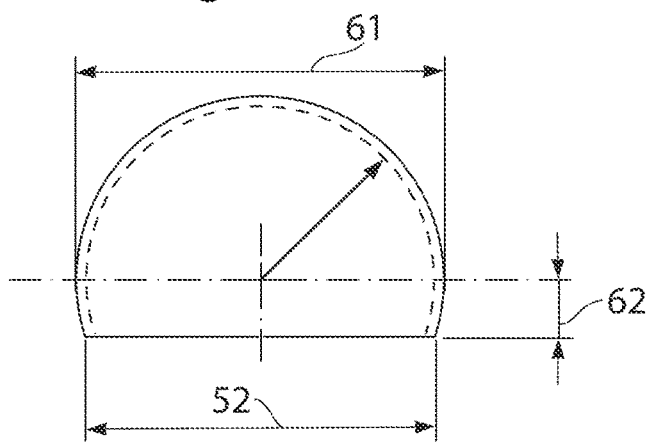
FIG. 31 shows, schematically, the artificial acetabulum or artificial caput femur.
Figure 32A:
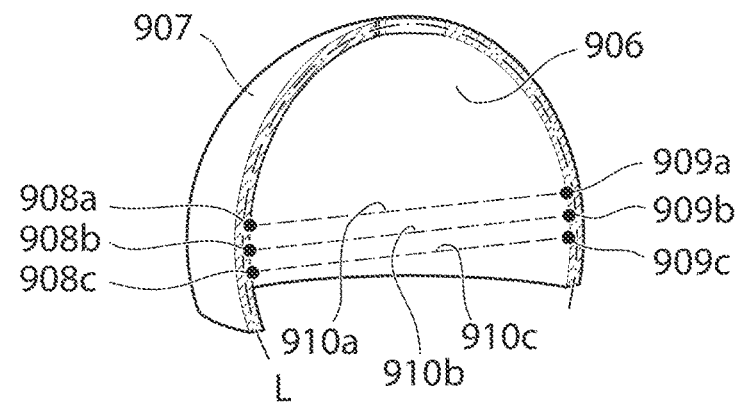
FIG. 32a shows the artificial acetabulum or artificial caput femur, in section.
Figure 32B:
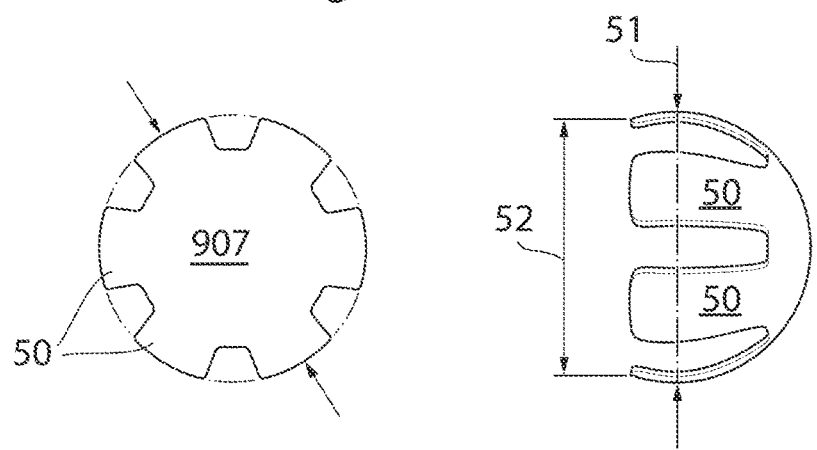
FIG. 32b shows an alternative embodiment.

FIG. 31 shows, schematically, how the artificial acetabulum travels beyond the maximum diameter of the caput femur 5, or an artificial replacement therefore. That is, a cross-sectional distance of the largest opening 52 is smaller than the largest cross sectional distance of the caput femur 5 or an artificial replacement therefore FIG. 32 shows the medical device according to an embodiment in which the second piece comprises: an inner surface 906, and an outer surface 907. The inner surface 906 comprises: a first point 908a, a second point 909a, a third point 908b, a fourth point 909b, a fifth point 908c, and a sixth point 909c, all points located on different places along a length axis of the inner surface. A first straight line 910a, reaches from the first point 908a to the second 909a and is parallel to a second straight 910b line reaching from the third point 908b to the fourth point 909b, which in turn is parallel to a third straight 910c line, reaching from the fifth point 908c to the sixth point 909c. The first 910a and the third 910c straight lines are shorter than the second straight line, and the second straight line is positioned between the first and third straight lines.

Opposite Embodiment

A general version of an opposite embodiment will now be described, the scope of the opposite embodiment is by no means limited to this particular version, on the contrary all of the above described embodiment can be used in the opposite embodiment.

Figure 33:
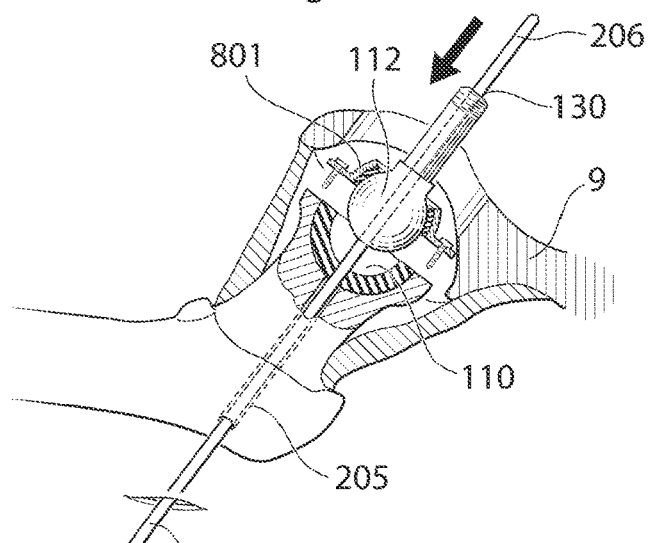
FIG. 33 shows the principle of an alternative embodiment.

FIG. 33 shows the hip joint in section when an artificial caput femur surface 112 is fixated to a surgically modified caput femur comprising a concave artificial acetabulum surface 110 placed in the surgically modified caput femur. According to the embodiment shown in FIG. 33 an elongated member 206 is used as a guiding rod, guiding and centering the artificial acetabulum surface, and the artificial caput femur surface in the hip joint. The convex hip joint surface 112 is secured by the releasing member 801 which is adapted to, in a first state, hold the artificial caput femur, and in a second state release the artificial caput femur, and change from a first to a second state when a pre-determined strain is exceeded. The releasing member is fixated to the surgically modified caput femur using screws 121. The surface of the locking element 117 and the concave hip joint surface 117 is placed in connection with the convex hip joint surface and could be made of a friction reducing material such as PTFE or a self lubricating powder material. However it is also conceivable that the connecting surfaces are lubricated using an implantable lubrication system adapted to lubricate the medical device after said medical device has been implanted in the human patient, a solution conceivable in all of the above described embodiments. According to the embodiment shown the elongated member 206 is inserted through the femoral bone, however according to other embodiments, not shown, the elongated member is positioned inside of the hip joint from the acetabulum side.

Figure 34:
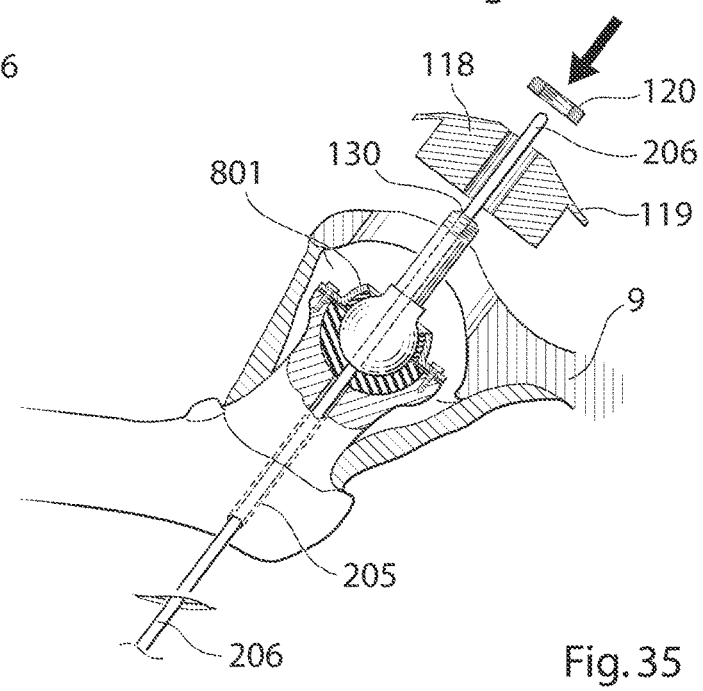
FIG. 34 shows the principle of an alternative embodiment.

FIG. 34 shows the placing of a prosthetic part 118 adapted to occupy the hole 18 created in the pelvic bone 9. The prosthetic part 118 comprises supporting members 119 adapted to be in contact with the pelvic bone 9 and assist in the carrying of the load placed on the medical device from the weight of the human patient. Furthermore FIG. 34 shows the fixation of a nut 120 to the attachment rod 113, which in turn is guided by the elongated member 206 which acts as a guiding rod.

Figure 35:
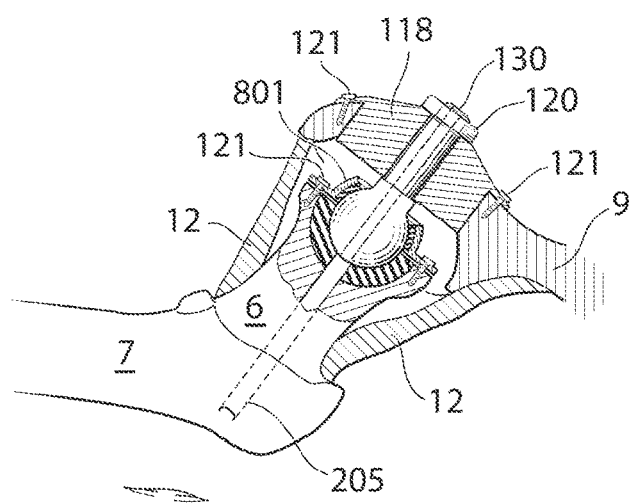
FIG. 35 shows the principle of an alternative embodiment.

FIG. 35 shows the hip joint in section when all the elements of the medical device has been fixated in the area of the hip joint or its surroundings. The prosthetic part 113 adapted to occupy the hole 18 in the pelvic bone 9 is here fixated with screws 121, however these screws 121 could be assisted or replaced by an adhesive which could be applied to the surface S between the prosthetic part and the pelvic bone 9. The elongated member 206 which acts as a guiding rod has been retracted through the incision in the thigh.

The elastic or flexible part, piece or portion of any of the embodiments herein could comprise an elastic polymer material such as: a copolymer material such as polystyrene, poly(ethylene-butylene) or polystyrene. It is also conceivable that the material is a polyurethane elastomeric material, polyamide elastomeric materials and polyester elastomeric materials elastic copolymers of ethylene and at least one vinyl monomer such as, for example, vinyl acetates, unsaturated aliphatic monocarboxylic acids, and esters of such monocarboxylic acids. The elastic band 813 could comprise a barrier coating, which cannot be penetrated by body cells. Preferably, the barrier coating comprises a Parylene™ coating, or a biocompatible metal coating, such as gold, silver or titanium. According to other embodiments the elastic band comprises a spring type member, a combination of metal and plastic materials, a combination of metal and carbon based material or a combination of carbon and plastic based material.

The artificial acetabulum, according to any of the embodiments, could comprise one or more parts which could be fixated to the pelvic bone using at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members.

Please note that any embodiment or part of embodiment as well as any method or part of method could be combined in any way. All examples herein should be seen as part of the general description and therefore possible to combine in any way in general terms.

The invention claimed is:

1. A method of installing a medical device for reducing the risk of permanent damage to a hip joint of a human patient, said method comprising the steps of:
   a. exposing the hip joint through a surgical or arthroscopic procedure,
   b. fixating a first piece of said medical device to the femoral bone,
   c. fixating a second piece of said medical device to the pelvic bone,
   d. placing said first piece in connection with said second piece, and
   e. holding said first piece to said second piece using a releasing member, and
   f. releasing said first piece from said second piece when a pre-determined strain is placed on said releasing member,
      wherein holding said first piece to said second piece using said releasing member comprises holding said first piece to said second piece using an elastic member, wherein said releasing elastic member is pretensioned in a direction towards a center axis running through the hip joint.

2. The method according to claim 1, holding said first piece to said second piece using said releasing member comprises holding said first piece to said second piece using a rupturing member.

3. The method according to claim 1, wherein holding said first piece to said second piece using said releasing member comprises holding said first piece to said second piece using a spring loaded member.

4. The method according to claim 1, wherein the step of holding said first piece to said second piece using said elastic member comprises holding said first piece to said second piece using an elastic band.

5. The method according to claim 2, wherein the step of holding said first piece to said second piece using said rupturing member comprises holding said first piece to said second piece using a rupturing band.

6. The method according to claim 1, further comprising the step:
   g. reinstating a prosthetic hip joint in an acetabulum or prosthetic acetabulum after releasing a prosthetic caput femur from the acetabulum or prosthetic acetabulum, when a strain, exceeding a predetermined threshold, is exerted on the hip joint.

7. The method according to claim 1, wherein the releasing member assumes a compressed state in response to said strain.

8. The method according to claim 1, wherein the releasing member comprises an elastic portion being at least partly formed of an elastic material.

9. The method according to claim 1, wherein the releasing member comprises a movable element.

10. The method according to claim 1, wherein the releasing member comprises a bendable portion and/or flexible portion and/or compressible portion and/or movable portion.

11. The method according to claim 1, wherein the releasing member comprises a first and a second element wherein at least one of the first and the second element moves in relation to the other element so as to allow the artificial caput femur to be released from an acetabulum or prosthetic acetabulum when a pre-determined strain is placed on said releasing member.

12. The method according to claim 11, wherein at least one of the first and second element are spring loaded to assist the movement of at least one of the first and second element.

13. The method according to claim 11, wherein at least one of the first and second elements are flexible.

14. The method according to claim 11, wherein the first and second element at least partly forms a spherical portion.

15. The method according to claim 1, wherein the releasing member comprises a rupture device adapted to break at a strain exceeding a threshold, so as to release an artificial caput femur from an acetabulum or an prosthetic acetabulum.

* * * * *